(12) United States Patent
Rodammer et al.

(10) Patent No.: US 12,142,374 B2
(45) Date of Patent: Nov. 12, 2024

(54) APPARATUSES, SYSTEMS, AND METHODS FOR INCREASING MOBILE APPLICATION USER ENGAGEMENT

(71) Applicant: Click Therapeutics, Inc., New York, NY (US)

(72) Inventors: Katie Nicole Rodammer, New York, NY (US); Caroline Pena, New York, NY (US)

(73) Assignee: Click Therapeutics, Inc., New York, NY (US)

( * ) Notice: Subject to any disclaimer, the term of this patent is extended or adjusted under 35 U.S.C. 154(b) by 527 days.

(21) Appl. No.: 17/286,031

(22) PCT Filed: Dec. 30, 2020

(86) PCT No.: PCT/US2020/067588
§ 371 (c)(1),
(2) Date: Apr. 16, 2021

(87) PCT Pub. No.: WO2021/138507
PCT Pub. Date: Jul. 8, 2021

(65) Prior Publication Data
US 2022/0399108 A1  Dec. 15, 2022

Related U.S. Application Data

(60) Provisional application No. 62/955,011, filed on Dec. 30, 2019.

(51) Int. Cl.
*G16H 40/63* (2018.01)
*G06F 3/0482* (2013.01)

(52) U.S. Cl.
CPC .......... *G16H 40/63* (2018.01); *G06F 3/0482* (2013.01)

(58) Field of Classification Search
CPC .............................. G16H 40/63; G06F 3/0482
See application file for complete search history.

(56) References Cited

U.S. PATENT DOCUMENTS

| 11,153,156 B2 * | 10/2021 | Jain ......................... G06N 3/08 |
| 11,520,607 B2 * | 12/2022 | Wayne .................. G06F 3/0482 |
| 2012/0042261 A1 * | 2/2012 | Phillips .................. G06F 9/542 |
| | | 715/744 |

(Continued)

*Primary Examiner* — Tadesse Hailu
(74) *Attorney, Agent, or Firm* — Bochner PLLC; Andrew D. Bochner

(57) ABSTRACT

A computer implemented method for increasing mobile application user engagement in a remote computing environment is provided. The method includes presenting a first popup window to a user including a first plurality of action buttons, a first of the first plurality of action buttons causing a change to a first attribute category to a first instantiation, and a second of the first plurality of action buttons causing a change to a second attribute category to a second instantiation, the first attribute category and the second attribute category comprising a type of attribute category of a second popup window; and subsequent to the presenting the first popup window to the user, presenting the second popup window to the user including a first instantiation if the first of the first plurality of action buttons was selected, and a second instantiation if the second of the first plurality of action buttons was selected.

20 Claims, 14 Drawing Sheets

(56) References Cited

U.S. PATENT DOCUMENTS

| | | | |
|---|---|---|---|
| 2012/0290974 A1* | 11/2012 | Doig | G06F 16/958 |
| | | | 715/808 |
| 2013/0167081 A1* | 6/2013 | Park | G06F 3/04817 |
| | | | 715/804 |
| 2013/0335335 A1* | 12/2013 | Neelakant | G06F 3/0486 |
| | | | 345/173 |
| 2016/0203275 A1* | 7/2016 | Benjamin | G06F 3/04817 |
| | | | 705/2 |
| 2019/0243944 A1* | 8/2019 | Jain | G16H 80/00 |

* cited by examiner

Database Structure

```
{
    "font_colors": ["#fff"],
    "bg_colors": ["#409dff", "#66c23a", "#8f9299", "#e6a13b", "#f66c6b"],
    "bd_width": [1, 2, 3, 4, 5],
    "fonts": ["Calibri", "Consolas", "Arial"],
    "font_sizes": [10, 11, 12, 13, 14],
    "canvas_image_forms": ["square", "circle", "triangle"],
    "canvas_movement_forms": ["vertical", "horizontal"],
    "opacities": [0, 50, 100],
    "sounds": ["sound1.mp3", "sound2.mp3"],
    "images": ["image1.jpg", "image2.jpg", "image3.jpg"],
    "button_positions": ["left", "right", "center"],
    "button_forms_width": [20, 40, 60, 80],
    "button_forms_height": [3, 4],
    "button_font_sizes": [10, 11, 12, 13, 14],
    "button_font_colors": ["#fff"],
    "button_bg_colors": ["#409dff", "#66c23a", "#8f9299", "#e6a13b", "#f66c6b"],
    "button_fonts": ["Calibri", "Consolas", "Arial"],
    "texts": ["text1.txt", "text2.txt", "text3.txt"]
}
```

FIG. 3A algorithms app/core.py from time import sleep from tkinter import * from PIL import ImageTk, Image import json import random from pygame import mixer import threading import tkinter.font as font class App:

text = ""

pillImage = None canvas_image_type = ""

image = None canvas_frame = None media_frame = None text_frame = None button1 = None button2 = None def __init__(self):

"""

Initialization function of the application where we initialize audio components and get parameters from the config file.

"""

*FIG. 3B* mixer.init(44100) # init audio component self.root = Tk() # create root of app build parameters self.data = self.buildParameters()

self.text_frame = Toplevel(self.root)

self.pillImage = Image.open('data/images/' + self.getParam('images'))

self.image = ImageTk.PhotoImage(self.pillImage)

self.canvas_image_type = self.getParam('canvas_image_forms')

self.text = self.getParam('texts')

def buildTextFrame(self):
"""

Function which builds a text popup and starts a new thread.

"""

"""

build text popup

:return: void

"""

self.text_frame.title('Text Frame') # create frame self.text_frame.minsize(width=400, height=400)

self.text_frame.config(background="white")

create component styles from parameters b_font = font.Font(weight='bold', size=self.getParam('font_sizes'), family=self.getParam('fonts'))

t_font = font.Font(weight='normal', size=self.getParam('font_sizes'), family=self.getParam('fonts'))

*FIG. 3C*

```
# create text widget
text = Text(self.text_frame,
        width=50,
        height=20,
        font=t_font,
        background=self.getParam('bg_colors'),
        foreground=self.getParam('font_colors'),
        borderwidth=self.getParam('bd_width'))

# create button widgets
self.button1 = Button(self.text_frame,
        width=self.getParam('button_forms_width'),
        height=self.getParam('button_forms_height'),
        text="Element",
        justify=self.getParam('button_positions'),
        background=self.getParam('button_bg_colors'),
        font=b_font,
        foreground=self.getParam('button_font_colors'),
        activebackground=self.getParam('button_bg_colors'),
        activeforeground=self.getParam('button_font_colors'))
self.button1.config(state=DISABLED)
self.button2 = Button(self.text_frame,
        width=self.getParam('button_forms_width'),
        height=self.getParam('button_forms_height'),
        text="Media",
```

*FIG. 3D*

```
            justify=self.getParam('button_positions'), background=self.getParam('button_bg_colors'), font=b_font, foreground=self.getParam('button_font_colors'), activebackground=self.getParam('button_bg_colors'), activeforeground=self.getParam('button_font_colors'))
        self.button2.config(state=DISABLED)

# read text from file and insert him to text frame
        f_text = open('data/texts/' + self.text, 'r')
        text.insert(1.0, f_text.read())
        text.pack()
        self.button1.pack()
        self.button2.pack()

# start new thread with changing button state function
        thread = threading.Thread(target=self.changeState)
        thread.start()

self.text_frame.protocol('WM_DELETE_WINDOW', self.on_closing) # set closing
protocol def buildCanvasFrame(self, event):
""""
    Function which renders geometry element based on data from the config file.
""""
        """"
```

*FIG. 3E* build popup with figure

:param event: tk button event

:return: void

"""

self.canvas_frame = Toplevel(self.root) # create frame self.canvas_frame.title('Canvas Frame')

self.canvas_frame.minsize(width=500, height=300)

self.canvas_frame.config(background="white")

self.canvas_frame.protocol('WM_DELETE_WINDOW', self.on_closing) # set closing protocol canvas = Canvas(self.canvas_frame, width=200, height=200, bg=self.getParam('bg_colors')) # create canvas widget type = self.getParam('canvas_image_forms') # get type of figure

_object = None build figure which based on getted type if type == 'square':

_object = canvas.create_rectangle(60, 80, 140, 190, fill=self.getParam('bg_colors'), outline=self.getParam('font_colors'), width=self.getParam('bd_width'), activedash=(5, 4))

elif type == 'circle':

_object = canvas.create_oval(50, 10, 150, 110, width=self.getParam('bd_width'), fill=self.getParam('bg_colors'), outline=self.getParam('font_colors'), )

elif type == 'triangle':

canvas.create_polygon((100, 10), (20, 90), (180, 90),

*FIG. 3F*

```
                fill=self.getParam('bg_colors'),
                outline=self.getParam('font_colors'),
                width=self.getParam('bd_width'),
                activedash=(5, 4))
    else: # if all conditions return 0 build rectangle
        _object = canvas.create_rectangle(60, 80, 140, 190,
                fill=self.getParam('bg_colors'),
                outline=self.getParam('font_colors'),
                width=self.getParam('bd_width'),
                activedash=(5, 4))
    canvas.pack()
    self.text_frame.destroy() # destroy frames
def buildMediaFrame(self, event):
    """

Function which displays media popup with image or plays sound.
    """

"""
    build media popup
    :param event: tk button event
    :return: void
    """
    if random.randint(0, 1): # is image?
        self.media_frame = Toplevel(self.root) # create frame
        self.media_frame.title('Media Frame')
        self.media_frame.minsize()
        self.media_frame.config(background="white")
```

*FIG. 3G*

```
        self.media_frame.protocol('WM_DELETE_WINDOW', self.on_closing) # set
closing protocol sprite = Label(self.media_frame, image=self.image) # display image on popup sprite.pack(side="bottom", fill="both", expand="yes")

else:

sound = mixer.Sound('data/sounds/' + self.getParam('sounds')) # create sound
mixer instance sound.play() # play sound sleep(2)

self.root.destroy()

self.text_frame.destroy() # destroy frames def build(self):

"""

Function which builds application with early declared parameters and methods.
"""

""""

build app method

:return: void

""""

self.buildTextFrame() # build text frame self.root.withdraw() # hide root self.root.mainloop() # run app in main loop def buildParameters(self):

"""

Function which reads data from the config file and parses it to the dictionary type
"""

""""
```

*FIG. 3H* get parameters from document

:return: dict

"""

with open('data/config.txt') as f:  # read document with parameters data = f.read()

data = json.loads(data) # parse getted data return data def getParam(self, key):

"""

get param from data

:param key: str

:return: mixed

"""

return self.data[key][random.randint(0, len(self.data[key]) - 1)]

def on_closing(self):

"""

handler on WM_DELETE_WINDOW event

:return: void

"""

self.root.destroy()

def changeState(self):

"""

Function which is tied to a new thread and changes buttons state from DISABLED to ACTIVE.

"""

"""

Thread method which changes button state

*FIG. 3I*

:return: void

"""

sleep(5) # delay 5 sec bind methods to buttons events self.button1.bind('<Button-1>', self.buildCanvasFrame)

self.button2.bind('<Button-1>', self.buildMediaFrame)

set buttons state to active self.button1.config(state=ACTIVE)

self.button2.config(state=ACTIVE)

main.py from app.core import App

Press the green button in the gutter to run the script.

if __name__ == '__main__':

app = App() # create app instance app.build() # build app instance

*FIG. 3J*

APPARATUSES, SYSTEMS, AND METHODS FOR INCREASING MOBILE APPLICATION USER ENGAGEMENT

PRIORITY

The present application claims priority to U.S. Provisional Patent Application No. 62/955,011, which was filed in the United States Patent and Trademark Office on Dec. 30, 2019, the entire disclosure of which is incorporated herein by reference.

INTRODUCTION

Embodiments of the invention relate generally to an apparatus for determining whether users of software are actively engaged and interacting with a software application. Such software may include applications that may be running on an electronic device including a smartphone, tablet, or the like.

Some users may be using certain software, for example, apps on a smartphone, tablet, or other device, without due care and/or adequate engagement.

For example, users of apps or other software may not be carefully reading the prompts, not be carefully selecting their responses, not be paying attention to any images or storyline that may appear on their screens, not be responding to prompts or questions in a timely manner, responding to such prompts or questions too quickly, responding to prompts or questions without carefully reading them, and the like.

However, it may be particularly important that users are engaged, especially when use of such software is recommended and/or prescribed by a medical professional and/or other clinician for the diagnosis or treatment of certain conditions such as insomnia or smoking cessation.

It would be desirable, therefore, to provide apparatuses, systems and methods for determining whether users of certain software are actively engaged and interacting with a software application as directed by their medical professional and/or clinician.

BRIEF DESCRIPTION OF THE DRAWINGS

FIGS. 3A-3J show source code that can implement one or more aspects of an embodiment of the present invention;

While the invention is described with reference to the above drawings, the drawings are intended to be illustrative, and the invention contemplates other embodiments within the spirit of the invention.

DETAILED DESCRIPTION

The present invention will now be described more fully hereinafter with reference to the accompanying drawings which show, by way of illustration, specific embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as devices or methods. Accordingly, the present invention may take the form of an entirely hardware embodiment, an entirely software embodiment, or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrases "in one embodiment," "in an embodiment," and the like, as used herein, does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" includes plural references. The meaning of "in" includes "in" and "on."

It is noted that description herein is not intended as an extensive overview, and as such, concepts may be simplified in the interests of clarity and brevity.

All documents mentioned in this application are hereby incorporated by reference in their entirety. Any process described in this application may be performed in any order and may omit any of the steps in the process. Processes may also be combined with other processes or steps of other processes.

Figure 1:
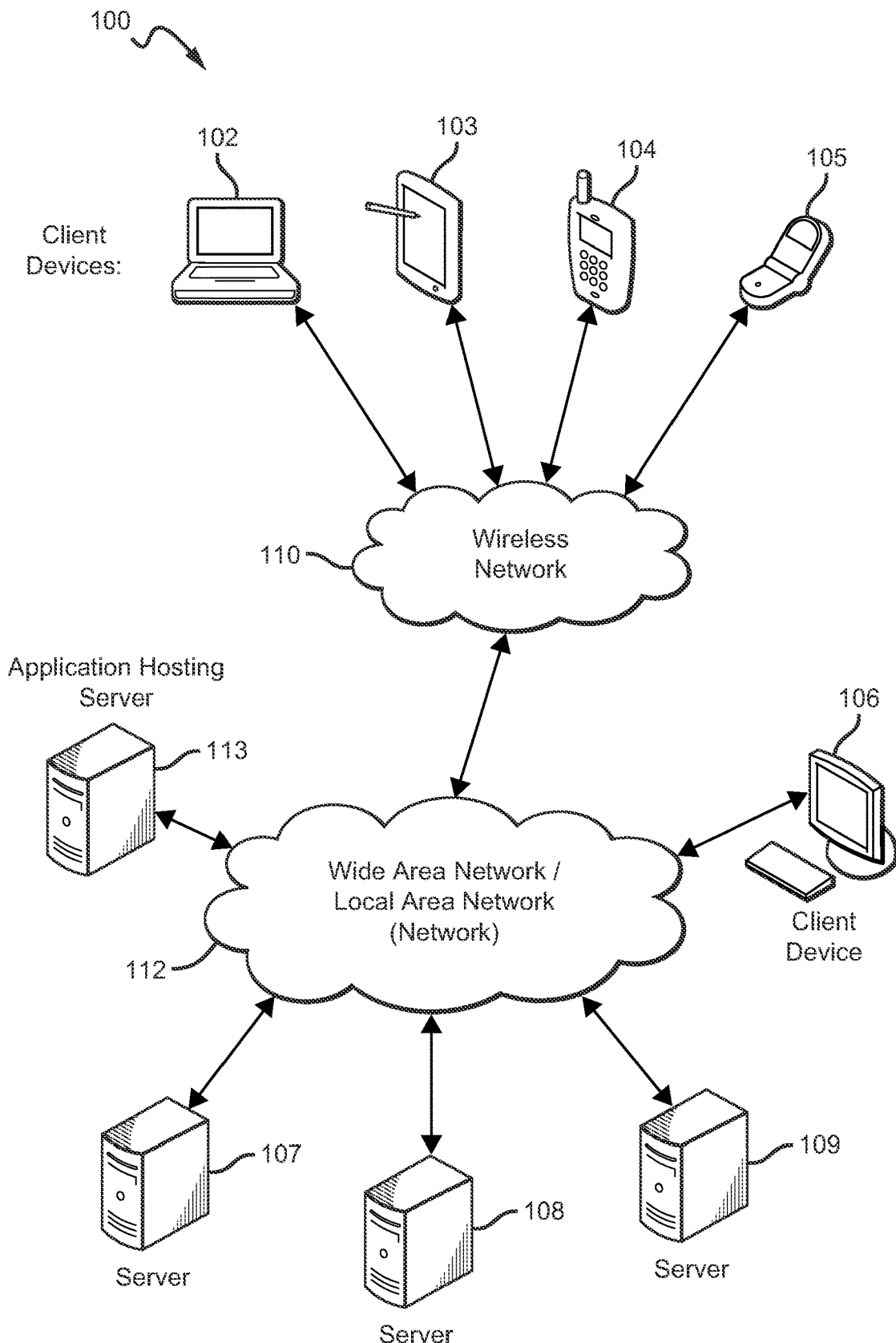
FIG. 1 illustrates a block diagram of a distributed computer system that can implement one or more aspects of an embodiment of the present invention.

FIG. 1 illustrates components of one embodiment of an environment in which the invention may be practiced. Not all of the components may be required to practice the invention, and variations in the arrangement and type of the components may be made without departing from the spirit or scope of the invention. As shown, the system 100 includes one or more Local Area Networks ("LANs")/Wide Area Networks ("WANs") 112, one or more wireless networks 110, one or more wired or wireless client devices 106, mobile or other wireless client devices 102-105, servers 107-109, and may include or communicate with one or more data stores or databases. Various of the client devices 102-106 may include, for example, desktop computers, laptop computers, set top boxes, tablets, cell phones, smart phones, smart speakers, wearable devices (such as the Apple Watch) and the like. Servers 107-109 can include, for example, one or more application servers, content servers, search servers, and the like. FIG. 1 also illustrates application hosting server 113.

Figure 2:
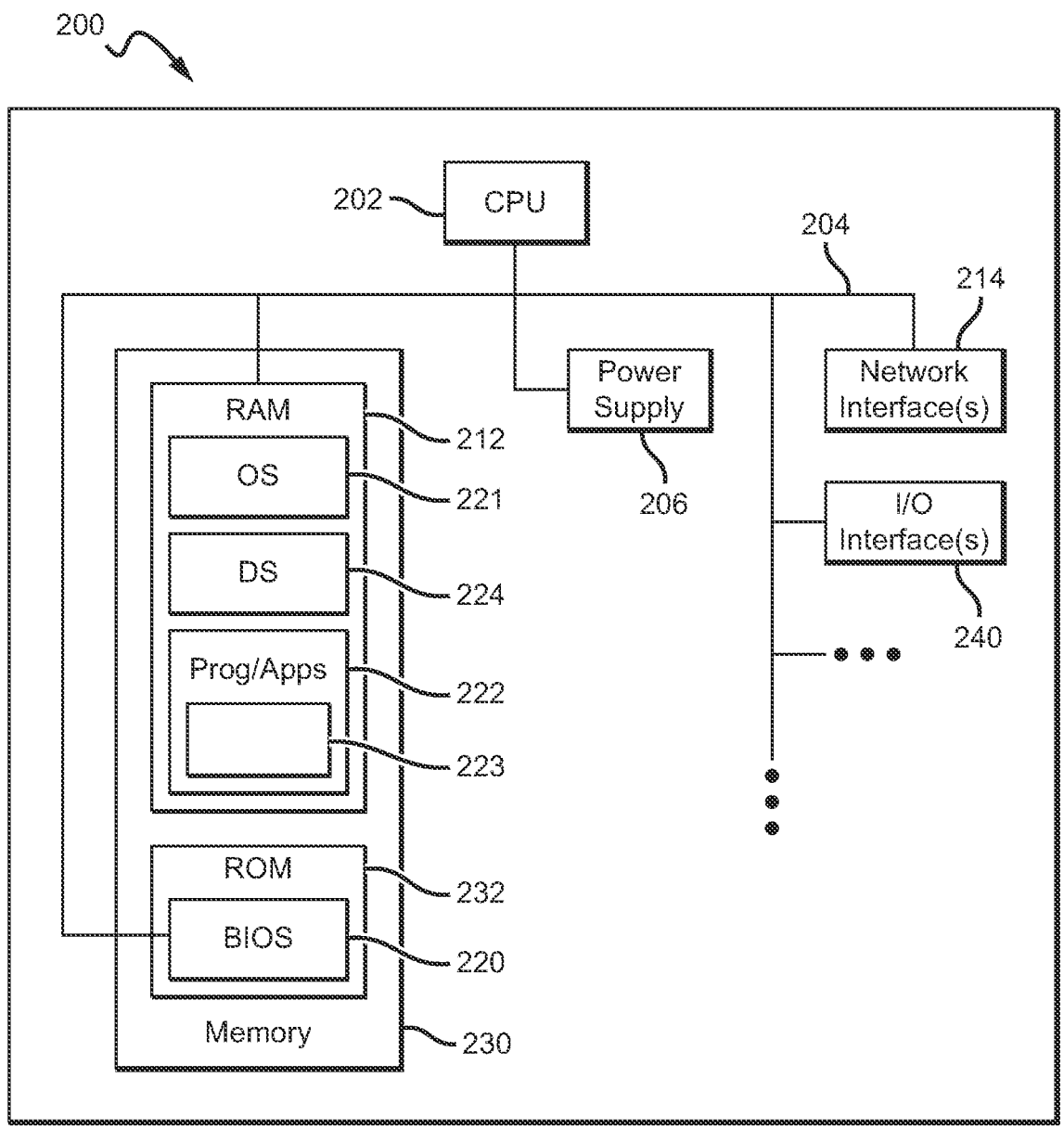
FIG. 2 illustrates a block diagram of an electronic device that can implement one or more aspects of an embodiment of the invention.

FIG. 2 illustrates a block diagram of an electronic device 200 that can implement one or more aspects of an apparatus, system and method for increasing mobile application user engagement (the "Engine") according to one embodiment of the invention. Instances of the electronic device 200 may include servers, e.g., servers 107-109, and client devices, e.g., client devices 102-106. In general, the electronic device 200 can include a processor/CPU 202, memory 230, a power supply 206, and input/output (I/O) components/devices 240, e.g., microphones, speakers, displays, touchscreens, keyboards, mice, keypads, microscopes, GPS components, cameras, heart rate sensors, light sensors, accelerometers, targeted biometric sensors, etc., which may be operable, for example, to provide graphical user interfaces or text user interfaces.

A user may provide input via a touchscreen of an electronic device 200. A touchscreen may determine whether a user is providing input by, for example, determining whether the user is touching the touchscreen with a part of the user's body such as his or her fingers. The electronic device 200 can also include a communications bus 204 that connects the aforementioned elements of the electronic device 200. Network interfaces 214 can include a receiver and a transmitter (or transceiver), and one or more antennas for wireless communications.

The processor 202 can include one or more of any type of processing device, e.g., a Central Processing Unit (CPU), and a Graphics Processing Unit (GPU). Also, for example, the processor can be central processing logic, or other logic, may include hardware, firmware, software, or combinations thereof, to perform one or more functions or actions, or to cause one or more functions or actions from one or more other components. Also, based on a desired application or need, central processing logic, or other logic, may include, for example, a software-controlled microprocessor, discrete logic, e.g., an Application Specific Integrated Circuit (ASIC), a programmable/programmed logic device, memory device containing instructions, etc., or combinatorial logic embodied in hardware. Furthermore, logic may also be fully embodied as software.

The memory 230, which can include Random Access Memory (RAM) 212 and Read Only Memory (ROM) 232, can be enabled by one or more of any type of memory device, e.g., a primary (directly accessible by the CPU) or secondary (indirectly accessible by the CPU) storage device (e.g., flash memory, magnetic disk, optical disk, and the like). The RAM can include an operating system 221, data storage 224, which may include one or more databases, and programs and/or applications 222, which can include, for example, software aspects of the program 223. The ROM 232 can also include Basic Input/Output System (BIOS) 220 of the electronic device.

Software aspects of the program 223 are intended to broadly include or represent all programming, applications, algorithms, models, software and other tools necessary to implement or facilitate methods and systems according to embodiments of the invention. The elements may exist on a single computer or be distributed among multiple computers, servers, devices or entities.

The power supply 206 contains one or more power components, and facilitates supply and management of power to the electronic device 200.

The input/output components, including Input/Output (I/O) interfaces 240, can include, for example, any interfaces for facilitating communication between any components of the electronic device 200, components of external devices (e.g., components of other devices of the network or system 100), and end users. For example, such components can include a network card that may be an integration of a receiver, a transmitter, a transceiver, and one or more input/output interfaces. A network card, for example, can facilitate wired or wireless communication with other devices of a network. In cases of wireless communication, an antenna can facilitate such communication. Also, some of the input/output interfaces 240 and the bus 204 can facilitate communication between components of the electronic device 200, and in an example can ease processing performed by the processor 202.

Where the electronic device 200 is a server, it can include a computing device that can be capable of sending or receiving signals, e.g., via a wired or wireless network, or may be capable of processing or storing signals, e.g., in memory as physical memory states. The server may be an application server that includes a configuration to provide one or more applications, e.g., aspects of the Engine, via a network to another device. Also, an application server may, for example, host a web site that can provide a user interface for administration of example aspects of the Engine.

Any computing device capable of sending, receiving, and processing data over a wired and/or a wireless network may act as a server, such as in facilitating aspects of implementations of the Engine. Thus, devices acting as a server may include devices such as dedicated rack-mounted servers, desktop computers, laptop computers, set top boxes, integrated devices combining one or more of the preceding devices, and the like.

Servers may vary widely in configuration and capabilities, but they generally include one or more central processing units, memory, mass data storage, a power supply, wired or wireless network interfaces, input/output interfaces, and an operating system such as Windows Server, Mac OS X, Unix, Linux, FreeBSD, and the like.

A server may include, for example, a device that is configured, or includes a configuration, to provide data or content via one or more networks to another device, such as in facilitating aspects of an example apparatus, system and method of the Engine. One or more servers may, for example, be used in hosting a Web site, such as the web site www.microsoft.com. One or more servers may host a variety of sites, such as, for example, business sites, informational sites, social networking sites, educational sites, wikis, financial sites, government sites, personal sites, and the like.

Servers may also, for example, provide a variety of services, such as Web services, third-party services, audio services, video services, email services, HTTP or HTTPS services, Instant Messaging (IM) services, Short Message Service (SMS) services, Multimedia Messaging Service (MMS) services, File Transfer Protocol (FTP) services, Voice Over IP (VOIP) services, calendaring services, phone services, and the like, all of which may work in conjunction with example aspects of an example systems and methods for the apparatus, system and method embodying the Engine. Content may include, for example, text, images, audio, video, and the like.

In example aspects of the apparatus, system and method embodying the Engine, client devices may include, for example, any computing device capable of sending and receiving data over a wired and/or a wireless network. Such client devices may include desktop computers as well as portable devices such as cellular telephones, smart phones, display pagers, Radio Frequency (RF) devices, Infrared (IR) devices, Personal Digital Assistants (PDAs), handheld computers, GPS-enabled devices tablet computers, sensor-equipped devices, laptop computers, set top boxes, wearable computers such as the Apple Watch and Fitbit, integrated devices combining one or more of the preceding devices, and the like.

Client devices such as client devices 102-106, as may be used in an example apparatus, system and method embodying the Engine, may range widely in terms of capabilities and features. For example, a cell phone, smart phone or tablet may have a numeric keypad and a few lines of monochrome Liquid-Crystal Display (LCD) display on which only text may be displayed. In another example, a Web-enabled client device may have a physical or virtual keyboard, data storage (such as flash memory or SD cards), accelerometers, gyroscopes, respiration sensors, body movement sensors, proximity sensors, motion sensors, ambient light sensors, moisture sensors, temperature sensors, compass, barometer, fingerprint sensor, face identification sensor using the camera, pulse sensors, heart rate variability (HRV) sensors, beats per minute (BPM) heart rate sensors, microphones (sound sensors), speakers, GPS or other location-aware capability, and a 2D or 3D touch-sensitive color screen on which both text and graphics may be displayed. In some embodiments multiple client devices may be used to collect a combination of data. For example, a smart phone may be used to collect movement data via an accelerometer and/or gyroscope and a smart watch (such as the Apple Watch) may be used to collect heart rate data. The multiple client devices (such as a smart phone and a smart watch) may be communicatively coupled.

Client devices, such as client devices 102-106, for example, as may be used in an example apparatus, system and method implementing the Engine, may run a variety of operating systems, including personal computer operating systems such as Windows, iOS or Linux, and mobile operating systems such as iOS, Android, Windows Mobile, and the like. Client devices may be used to run one or more applications that are configured to send or receive data from another computing device. Client applications may provide and receive textual content, multimedia information, and the like. Client applications may perform actions such as browsing webpages, using a web search engine, interacting with various apps stored on a smart phone, sending and receiving messages via email, SMS, or MMS, playing games (such as fantasy sports leagues), receiving advertising, watching locally stored or streamed video, or participating in social networks.

In example aspects of the apparatus, system and method implementing the Engine, one or more networks, such as networks 110 or 112, for example, may couple servers and client devices with other computing devices, including through wireless network to client devices. A network may be enabled to employ any form of computer readable media for communicating information from one electronic device to another. The computer readable media may be non-transitory. A network may include the Internet in addition to Local Area Networks (LANs), Wide Area Networks (WANs), direct connections, such as through a Universal Serial Bus (USB) port, other forms of computer-readable media (computer-readable memories), or any combination thereof. On an interconnected set of LANs, including those based on differing architectures and protocols, a router acts as a link between LANs, enabling data to be sent from one to another.

Communication links within LANs may include twisted wire pair or coaxial cable, while communication links between networks may utilize analog telephone lines, cable lines, optical lines, full or fractional dedicated digital lines including T1, T2, T3, and T4, Integrated Services Digital Networks (ISDNs), Digital Subscriber Lines (DSLs), wireless links including satellite links, optic fiber links, or other communications links known to those skilled in the art. Furthermore, remote computers and other related electronic devices could be remotely connected to either LANs or WANs via a modem and a telephone link.

A wireless network, such as wireless network 110, as in an example apparatus, system and method implementing the Engine, may couple devices with a network. A wireless network may employ stand-alone ad-hoc networks, mesh networks, Wireless LAN (WLAN) networks, cellular networks, and the like.

A wireless network may further include an autonomous system of terminals, gateways, routers, or the like connected by wireless radio links, or the like. These connectors may be configured to move freely and randomly and organize themselves arbitrarily, such that the topology of wireless network may change rapidly. A wireless network may further employ a plurality of access technologies including 2nd (2G), 3rd (3G), 4th (4G) generation, Long Term Evolution (LTE) radio access for cellular systems, WLAN, Wireless Router (WR) mesh, and the like. Access technologies such as 2G, 2.5G, 3G, 4G, and future access networks may enable wide area coverage for client devices, such as client devices with various degrees of mobility. For example, a wireless network may enable a radio connection through a radio network access technology such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, and the like. A wireless network may include virtually any wireless communication mechanism by which information may travel between client devices and another computing device, network, and the like.

Internet Protocol (IP) may be used for transmitting data communication packets over a network of participating digital communication networks, and may include protocols such as TCP/IP, UDP, DECnet, NetBEUI, IPX, Appletalk, and the like. Versions of the Internet Protocol include IPv4 and IPv6. The Internet includes local area networks (LANs), Wide Area Networks (WANs), wireless networks, and long-haul public networks that may allow packets to be communicated between the local area networks. The packets may be transmitted between nodes in the network to sites each of which has a unique local network address. A data communication packet may be sent through the Internet from a user site via an access node connected to the Internet. The packet may be forwarded through the network nodes to any target site connected to the network provided that the site address of the target site is included in a header of the packet. Each packet communicated over the Internet may be routed via a path determined by gateways and servers that switch the packet according to the target address and the availability of a network path to connect to the target site.

The header of the packet may include, for example, the source port (16 bits), destination port (16 bits), sequence number (32 bits), acknowledgement number (32 bits), data offset (4 bits), reserved (6 bits), checksum (16 bits), urgent pointer (16 bits), options (variable number of bits in multiple of 8 bits in length), padding (may be composed of all zeros and includes a number of bits such that the header ends on a 32 bit boundary). The number of bits for each of the above may also be higher or lower.

A "content delivery network" or "content distribution network" (CDN), as may be used in an example apparatus, system and method implementing the Engine, generally refers to a distributed computer system that comprises a collection of autonomous computers linked by a network or networks, together with the software, systems, protocols and techniques designed to facilitate various services, such as the storage, caching, or transmission of content, streaming media and applications on behalf of content providers. Such services may make use of ancillary technologies including, but not limited to, "cloud computing," distributed storage, DNS request handling, provisioning, data monitoring and reporting, content targeting, personalization, and business intelligence. A CDN may also enable an entity to operate and/or manage a third party's web site infrastructure, in whole or in part, on the third party's behalf.

A Peer-to-Peer (or P2P) computer network relies primarily on the computing power and bandwidth of the participants in the network rather than concentrating it in a given set of dedicated servers. P2P networks are typically used for connecting nodes via largely ad hoc connections. A pure peer-to-peer network does not have a notion of clients or servers, but only equal peer nodes that simultaneously function as both "clients" and "servers" to the other nodes on the network.

Embodiments of the present invention include apparatuses, systems, and methods implementing the Engine. Embodiments of the present invention may be implemented on one or more of client devices 102-106, which are communicatively coupled to servers including servers 107-109. Moreover, client devices 102-106 may be communicatively (wirelessly or wired) coupled to one another. In particular, software aspects of the Engine may be implemented in the program 223. The program 223 may be implemented on one or more client devices 102-106, one or more servers 107-109, and 113, or a combination of one or more client devices 102-106, and one or more servers 107-109 and 113.

Embodiments of the present invention, which may be implemented at least in part in the program 223, relate to apparatuses, systems and methods for increasing mobile application user engagement.

Disclosed herein are apparatuses, systems and methods for determining whether users of software are actively engaged and interacting with a software application.

Pharmaceuticals are most likely to provide beneficial results when taken as prescribed, and patient compliance/adherence to medical treatment as prescribed by a clinician is an established problem in both clinical trials and the real world.

Another form of treatment in which patient compliance/adherence is important is one that consists of or includes interaction with an electronic device such as a smartphone, tablet, laptop, or the like (i.e., Digital Therapeutics (DTx)). Such treatment may be complementary to or may replace a pharmaceutical treatment. For example, if a patient is addicted to smoking, a clinician may prescribe a treatment of interacting with software running on an electronic device that monitors smoking by the patient or otherwise interacts with the patient regarding smoking.

For example, the software may determine the location of the user by using location services (such as a GPS receiver and associated software) of the electronic device. If the software determines that the user is in a location where the user, and/or the population as a whole, and/or the user's demographic, is more likely to smoke, the software may take certain actions such as activating a camera, activating a microphone, activating sensors that can determine the presence of smoke, reminding the user not to smoke by generating a message on the screen of the electronic device, asking the user if he or she is smoking by generating a message on the screen of the digital device (including an answer prompt), calling the user with a prerecorded message, and the like.

However, a person that has been prescribed such treatment may simply "click through" any prompts and would thus not provide positive results. Moreover, simply clicking through or not being actively engaged would not provide accurate results as to the treatment's efficacy. For example, a user can easily click through an activity answering "yes" or "done" to activities that were never actually completed by the user (prompts not actually read by the user, tasks not performed by the user, and the like).

Embodiments of the present invention measure adherence of a given treatment by, for example, measuring the user's click speed as they navigate through the modules of the application. To bridge the gap between adherence and engagement, embodiments of the present invention include algorithms to personalize compliance remediation techniques based on user demographics, click speed, and baseline user habits.

To summarize, according to certain embodiments of the present invention, when a user begins clicking faster or slower than certain pre-defined thresholds, alerts and messages will appear in the app in order to: (1) attract the user's attention; (2) alert the user that the software is monitoring their behavior since users are generally more compliant when they believe they are being monitored; and (3) encourage the user to modify their behavior to engage more actively with the software. This results in a more compliant user and more successful treatment.

More specifically, once a user is prescribed the treatment (i.e., interaction with a DTx, a software/app running on an electronic device such as a smartphone), the user will first input basic demographic information (e.g., age, weight, location, health history, and the like). During the first two (2) (or 1 or 3 or 4) weeks of treatment, baseline user habits are first recorded by the software. These inputs will then be used to monitor threshold limits throughout the treatment. If a threshold is passed (e.g., user click speed is above or below a defined personal limit of that user), the software will deploy in-app alerts and messages to encourage the user to be more engaged with the product.

The in-app alerts and messages will be accessed from a library/database of messages, alerts, and educational information, stored either on the electronic device or on another device such as a server communicatively coupled with the electronic device. User response to the app (i.e., determining whether alerts were effective and whether the user is more or less engaged) is assessed by the software, and similar types of alerts will be used on an ongoing basis to promote user treatment engagement if the app determines that the thresholds have been passed. $\theta_n$ the other hand, if the software determines that alerts were ineffective, different alerts will be selected from the library/database to determine whether other alerts may be more effective at changing user behavior.

The following provides further detail regarding the software for determining whether users of software are actively engaged and interacting with a software application.

To quantify a user's engagement, an embodiment of the present invention first creates a user profile based on information collected from demographic questions and calculates baseline Click Speed (CS) values and Deviation Thresholds (DTs) for the user during the initial weeks (e.g., 2) of treatment. The software then detects when the CS, calculated as the user is interacting with the app, deviates above or below the DT. When deviations occur, users receive feedback in order to promote adherence and continued engagement with their treatment.

When a user first begins treatment, the user is asked questions about his or her age and physical disabilities. These factors are considered relevant when creating a baseline for a user as they could impact the speed at which a user interacts with a mobile app. For example, if a user is over 55 years old or has a physical disability that could affect their dexterity (such as brain or spinal cord injuries, cerebral palsy, arthritis, and more), the user may interact with a mobile app slower than an average person. The user's CS within the software is also recorded during this time and for the two weeks of treatment. CS is defined as the change in time according to the following equation (1): $CS = t_{C2} - t_{C1}$ According to the above equation (1), $t_{C2}$ is the time at which a user clicks on a feature (e.g., button, toggle, image, etc.) on a screen within the app and $t_{C1}$ is the time at which the user either first opened that screen (if $t_{C2}$ is the first time the user interacted with the screen since it was opened) or clicked on another feature (button, toggle, image, etc.) within that screen, if the user has already interacted with the screen.

Embodiments of the present invention include 2 types of program aspects that are relevant for treatment: (1) Missions, which are activities that mainly contain text for the user to read and some sections that require user interaction; and (2) Features, which are activities that mainly contain sections that require user interaction and some text. Because of their differences, CS is tracked for these two aspects separately as the speed at which a user interacts with them may differ.

In addition, time of day is also tracked, as users may exhibit differences in CS depending on time of day. For example, users may be more tired at 3 a.m. as opposed to 3 p.m. Thus, it is necessary to track the time of day and compare the user's CS to the baseline CS for that time of day.

These 2 considerations (differences in program aspects and time) lead to the creation of 6 CS baseline values per user: (1) $CS_{MM}$ (CS of interactions with Missions in the morning, or between the hours of 5 AM to 11:59:59 a.m. inclusive); (2) $CS_{MF}$ (CS of interactions with Features in the morning); (3) $CS_{AM}$ (CS of interactions with Missions in the afternoon, or between the hours of 12 p.m. to 5:59:59 p.m. inclusive); (4) $CS_{AF}$ (CS of interactions with Features in the afternoon); (5) $CS_{EM}$ (CS of interactions with Missions in the evening/night, or between the hours of 6 p.m. to 4:59:59 a.m. inclusive); and (6) $CS_{EF}$ (CS of interactions with DTx features in the evening/night). Deviation thresholds (DTs) were set to 5 seconds (faster or slower) per CS baseline as a default (i.e., Equation (2), DT for $CS = CS \pm 5$ seconds). However, if users indicated factors that would impact their CS in their user profile, DTs were adjusted using the following equation (3):

$$DT \text{ for } CS = CS \pm (5*(n+0.25)) \text{ seconds}$$

According to the above equation (3), CS is the click speed baseline value and n is the number of factors that could impact click speed that the user indicated in their profile in response to the initial question posed by the software.

For example, consider a user who is 30 years old with no physical disabilities, and has the following CS baseline values: $CS_{MM}$=62 seconds (s), 2; $CS_{MF}$=25 s, 3; $CS_{AM}$=50 s, 4; $CS_{AF}$=18 s, 5; $CS_{EM}$=55 s, 6; and $CS_{EF}$=20 s The DTs for the above would user would thus be as follows: DT for $CS_{MM}$=62±5 s, 2; DT for $CS_{MF}$=25±5 s, 3; DT for $CS_{AM}$=50±5 s, 4; DT for $CS_{AF}$=18±5 s, 5; DT for $CS_{EM}$=55±5 s, 6; DT for $CS_{EF}$=20±5 s.

That is, for example, with respect to $CS_{MM}$, applying equation (2), the result is 62±5 seconds.

However, if we had a user who had the same CS baseline values but was 60 years old and had arthritis (n=2) (i.e., +1 for being 55 years or older and +1 for having arthritis) their DTs would be: DT for $CS_{MM}$=62±11.25 s, 2. DT for $CS_{MF}$=25±11.25 s, 3. DT for $CS_{AM}$=50±11.25 s, 4. DT for $CS_{AF}$=18±11.25 s, 5. DT for $CS_{EM}$=55±11.25 s, 6. DT for $CS_{EF}$=20±11.25 s.

That is, for example, with respect to $CS_{MM}$, applying equation (3), 62±(5*(2+0.25)) s=62±11.25 s.

After the CS baseline values and DTs are calculated, comparisons between CS values are calculated each time the user interacts with the mobile app and DTs for the relevant time-of-day are made. Deviations from DTs are recorded for the user. For example, for the $CS_{MM}$ example for the 60 year old user with arthritis, discussed above, assuming the $CS_{MM}$ was more than 73.25 seconds or less than 50.75 seconds, a deviation would be determined and stored in a database, either on the electronic device or a database residing on a server communicatively coupled to the electronic device.

After a predetermined number (e.g., 3) of deviations are recorded for a user, a determination is made that the user is not properly engaging with the software. The user then receives a message randomly selected from a library containing alerts that warns the user of their behavior, and provides information on the importance of adhering to their treatment and humorous messages.

Some of the content in these messages is customized to the deviation behavior shown by the user (faster/slower clicks). For example, if the CS of the user discussed above is higher than 73.25 seconds, a message tailored for slow click speed is selected from the database. However, if the CS of the user discussed above is lower than 50.75 seconds, a message tailored for fast click speed is selected from the database.

The type of message displayed to the user on the screen of the electronic device is then recorded (e.g., alert, information, or humor).

After the first such message is displayed to the user, the software determines whether there is an ongoing problem of user engagement. If a predetermined number, e.g., 3, of additional deviations occur within the span of the next predetermined number, e.g., 7, of days, the user receives a message randomly selected from the other two types of messages. That is, for example, if the user was originally shown a message selected from the "humor" messages, either an "information" or an "alert" message would then be shown. This is so to attempt to determine a feedback method that would effectively promote user engagement on an individual basis. That is, if a "humor" message was not effective in promoting user engagement, it is then determined whether an "information" or "alert" message is effective.

For example, if the algorithm detects three deviations from a user and sends an information message to the user such as "Medication has best results when taken as prescribed. Likewise, engaging with this digital therapeutic is essential in ensuring you are receiving adequate treatment!" and 4 days later, the software detects another 3 deviations from the user, the user may then receive an alert message such as "You've been completing your missions faster than usual! Make sure you're reading through the missions completely!"

If, after the "alert" message, the user's CS does not deviate from the DTs for the next 7 days, the software would record alert messages as being an effective form of feedback method for promoting engagement. The software would also record that the "information" message is not an effective form of feedback method for promoting engagement. Thus, if the user then again begins to deviate from DTs, they would receive another "alert" message since it has been determined that alert messages are more effective than information messages.

The above embodiments generally relate to using CS to determine whether the user is adequately engaged. However, other factors may be used instead of or in conjunction with user CS.

For example, software running on an electronic device may determine the proportion of the time a user is looking at the relevant portion of the electronic device screen (i.e., eye tracking). For example, some smartphones allow picture-in-picture functionality, where the user may be interacting with one app (e.g., watching a movie or a TV show in the Netflix app) while also interacting with another app (e.g., an app prescribed by a clinician). In this case, although the CS may indicate that the user is actively engaged with the app prescribed by the clinician, the user may in fact have spent a portion of that time engaged with another app. That is, for example, if the app prescribed by the clinician is in a particular portion of the screen (e.g., the upper right quadrant), the app can determine that 80% of the relevant CS time was actually spent looking at the upper left, lower left, and/or lower right quadrants, engaging with another app such as Netflix.

In order to make the above determination, the app accesses a camera on the electronic device or another camera near the user, which takes one or more photographs or videos of the user, determines the location of the sclera, iris, pupil and other parts of one or both of the eyes of the user. The software takes regular photographs (for example, every 1 second or 0.5 seconds) and determines the point on the screen of the electronic device at which one or both eyes are focused. Once the point on the screen is determined, the software uses certain Application Programming Interfaces (APIs) provided by the electronic device to determine the app the user is focused on. The software then calculates the proportion of points the user was focused on that are on the clinician prescribed app. If the proportion of points is below a certain threshold (e.g., 75%), a determination is made that the user is not engaging with the clinician prescribed app.

In another embodiment, the software running on the electronic device may take multiple photos to determine whether the user is in motion. For example, the software may determine that the user is running or engaged in another activity during which the user would be unlikely to be actively engaged with the clinician prescribed app.

In yet another embodiment, the software running on the electronic device may activate a microphone to determine sounds that may make it unlikely that the user is actively engaged with the clinician prescribed software. For example, when determining user baselines, the app may record the user's voice. The app may then determine, by activating the microphone on the electronic device, whether the user is speaking, other people are speaking, music is playing, the user is attending an event, and the like. If the app determines that the user was speaking more than a certain proportion of the time, the app would determine a deviation.

In yet another embodiment, a machine learning-based algorithm may be used to quantify a user's engagement with a certain app running on an electronic device such as a smartphone (e.g., an app that is or includes a DTx). Specifically, in order to quantify a user's engagement, a regression tree-based algorithm is utilized to predict a user's time spent (TS) on each program aspect of a digital therapeutic (DTx) relying on demographics. The algorithm then detects when a particular user's TS deviates above or below the predicted average time spent (ATS) for the user when interacting with a particular program aspect. When deviations occur, a user receives feedback in order to promote adherence and continued engagement with their treatment. That is, once a particular user's demographic information is known (e.g., age, sex, location), a predicted ATS, relying on data from past interactions by other users of the same and/or similar demographics, is generated and a predicted ATS is determined for that user. That predicted ATS is then compared to the user's actual ATS (or TS) when interacting with various features of the DTx. If the predicted ATS is substantially different than the actual ATS (or TS), the DTx may determine that a user is not properly engaging with the DTx or particular aspects thereof. For example, if the actual ATS is substantially longer than the predicted ATS for a particular aspect, the user may have stopped interacting with the particular aspect of the DTx for a certain period of time (e.g., while watching television, using another app, speaking to someone, and the like). In the alternative, if the actual ATS is substantially shorter than the predicted ATS for a particular feature, the user may have interacted with the particular aspect of the DTx without actively engaging with such aspect (e.g., the user may not have been reading the prompts and/or following directions provided by the aspect and was simply "clicking through" to give the illusion that they completed interacting with such feature). A more detailed discussion is provided below.

First, a DTx data platform is utilized in order to develop and train the predictive model. The platform collects data from its users including demographic information provided by users when a profile is first set up (for example, age, sex, and location of a user) and a user's activity and interaction with the DTx. In the alternative, demographic information about a user may be obtained from other sources such as information obtained from publicly available databases, background checks, medical data, finding and crawling a user's social media accounts, and the like. For example, in crawling a user's social media accounts, certain proxies may be used to determine a user's demographic information. For example, if a user uses particular words in their social media posts that are more likely to be used by a certain age demographic (e.g., millennials), it may be assumed such a user's age is that of a millennial (e.g., an average millennial age may be assumed). Similarly, if a user "likes" or comments on a particular musical band, that a particular demographic (such as age) is more likely to listen to, it may be assumed that that user is part of that demographic. As another example, if a user likes or comments about a cause that is more likely to be supported by a particular demographic (such as a particular sex), it may be assumed that that user is part of that demographic.

Once a user's demographics are obtained and stored, time stamps of when a particular user first begins using a program aspect are collected and stored in a database (the database may be stored on the electronic device, such as a smartphone, or on a server communicatively coupled to the electronic device). Also, time stamps of when a particular user stops begins using a program aspect are collected and stored in a database.

As noted above, DTx programs may include 2 types of program aspects that are relevant for treatment: (1) Missions, which are activities that mainly contain text, and some sections that require user interaction; and (2) Features, which are activities that mainly contain sections that require user interaction, and some text. Missions and Features can also differ on a Mission-to-Mission or Feature-to-Feature basis, depending on the treatment and the specific DTx. For example, some missions may range from including several sentences of information and no user interaction (e.g., a mission may include a user learning about their treatment and how a DTx can benefit them, with little to no user interaction) to being based only on receiving user input (e.g., a user selecting goals from a list and saving them). Some Features can range from requiring only one input from the user (i.e., user inputs their mood into the app (e.g., happy, sad, anxious, excited, and the like) to requiring a user's attention and participation for a set period of time (e.g., asking the user to participate in a physical activity such as a 5-minute long breathing exercise). Because of this, time stamp data is extracted and analyzed from an individual program aspect basis. From the time stamp data, time spent (TS) on a program aspect, n, was defined as the change in time (Equation 4):

$$TS_n = t_2 - t_1$$

In Equation 4, shown above, $t_2$ is the time stamp of when a user begins using a program aspect and $t_1$ is the preceding time stamp of when a user begins using a different program aspect, not accounting for idle time (i.e, when application is not in active use). In situations where a user first opened the app, their TS would be calculated by (Equation 5):

$$TS_n = t_2 - t_0$$

In Equation 5, shown above, $t_2$ is the time stamp of when a user begins using a program aspect and to is the time stamp of when a user first opens the DTx. For example, if a user logged their mood using the DTx at 5:30 p.m., began Mission 1 at 5:32 p.m., which they then finished at 5:40 p.m., their TS for the log mission feature would be 2 minutes and their TS for Mission 1 would be 8 minutes. That is, to calculate the TS for Mission 1, using Equation 4, $TS_n = t_2 - t_1$, $t_2$ would be equal to 5:40 p.m., $t_1$, would be equal to 5:32 p.m., thus, $TS_n$ for Mission 1 would be 8 minutes.

Regression trees (a type of Decision Tree) may be constructed for each predictor. That is, various user demographics that are considered predictors for TSs for each program aspect are collected including age, sex, and location. These predictors are then used to construct regression trees. Regression trees are constructed for each predictor (e.g., age, sex, and location). This allows for the interpretation of the most important predictor thresholds and splits. In each tree, different thresholds are tested for age (e.g., ranging from 18 to over 65 years old age), sex (e.g., female or male) and location (e.g., divided into the 5 regions of the United States: West, Southwest, Northeast, Southeast, and Midwest) and the threshold for each predictor that results in the minimum sum of squared residuals (SSR), deviations from empirical data, is selected as a candidate. When examining one predictor, SSR is given by the following equation:

$$SSR = \sum_{i=1}^{n}(y_i - x_i)^2$$

where $y_i$ is the observed average value of the variable to be predicted and $x_i$ is the predicted value. In other words, SSR quantifies the quality of the predictions. The SSR for each candidate is then compared and the candidate with the lowest SSR becomes the root of the tree model (for example, age>=65 in the regression tree shown in FIG. 5). The rest of the tree is then constructed by comparing the lowest SSR of each predictor. Given a user's age, sex, and location, the algorithm then predicts their TS on a specific program aspect. For example, if the thresholds with the lowest SSR values within the predictor groups were as follows:
 1. Age>=65 (SSR=11,465)
 2. Sex=Female (SSR=18,345)
 3. Location=West (SSR=19,642)

Figure 5:
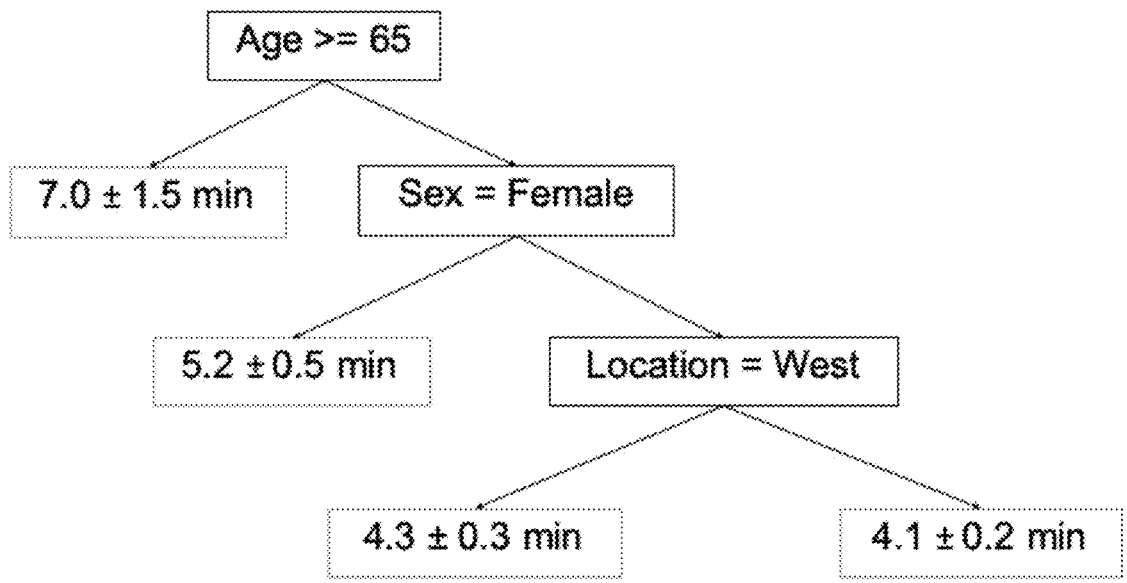
FIG. 5 illustrates an example of a regression tree as contemplated by one or more embodiments of the present invention.

Age>=65 would become the root of the tree as it has the lowest SSR value compared to the other two thresholds. The lowest SSR values from each predictor group is compared to grow the tree. FIG. 5 is an example of a short regression tree for Mission 1, considering all predictors.

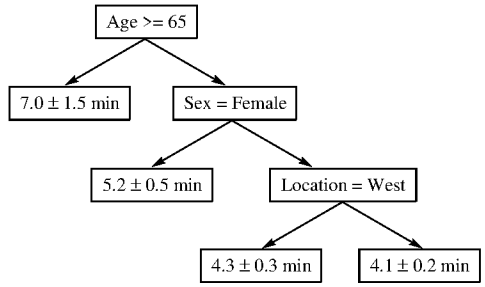

Once a regression tree, such as the one in FIG. 5, is generated, it may be used to determine the predicted ATS for a particular user. For example, if the particular user is a 64 year male who lives in the Northeast, the regression tree would be traversed as follows. First, the decision point at the root would be evaluated. In this case, if the user had an age of >=65 the predicted ATS would be 7.0±1.5 minutes. That is, if the user had an age of >=65, the predicted ATS would be between 5.5 and 8.5 minutes, inclusive. However, in our case, since the particular user is 64 years old, the algorithm proceeds to the right to the second decision point. The second decision point determines whether the sex of the particular user is female and, since the user is not female, the algorithm proceeds to the right to determine whether the particular user lives in the West. Since the user does not live in the West, the result of the tree traversal is 4.1±0.2 minutes, or between 3.9 and 4.3 minutes inclusive. Thus, a 64 year old male who lives in the Northeast would have a predicted ATS of between 3.9 and 4.3 minutes, inclusive. However, if the user was a 64 year old male who lives in the West, the algorithm would operate similarly, except at the last decision point, would evaluate to true and result in 4.3±0.3 minutes, or between 4.0 and 4.6 minutes, inclusive.

After a user's TS for a specific program aspect was predicted, comparisons between the predicted value and calculated TS value are made. Deviations from the predicted value are then recorded for the user. After three deviations are recorded for a user, the user receives a message randomly selected from a library of containing alerts that warn them of their behavior, information on the importance of adhering to their treatment, and humorous messages. Some of the content in these messages would be customized to the deviation behavior shown by the user (faster/slower than the predicted TS). The type of message shown is then recorded (alert, information, or humor). If three (or another predetermined number) more deviations occur within the span of a predetermined number of days (e.g., 7 days), the user receives a message that is randomly selected from one of the other two types of messages. This is done to determine a feedback method that would effectively promote user engagement on an individual basis.

For example, if the algorithm detected three deviations from a user within a predetermined period of time and sent an information message such as: "Medication has best results when taken as prescribed. Likewise, engaging with this digital therapeutic is essential in ensuring you are receiving adequate treatment!" and 4 days later, the algorithm detects another three deviations, the user may receive an alert message such as: "You've been completing your missions faster than usual!Make sure you're reading through the missions completely!" However, if the user's CS does not deviate from the DTs for the next 7 days, the algorithm would record alert messages as being an effective form of feedback method for promoting engagement. If the user then began to deviate from DTs after this time span, they would receive another alert message.

In yet another embodiment, another machine learning-based algorithm may be used to quantify a user's engagement with a certain app running on an electronic device such a smartphone (e.g., an app that is or includes a DTx). Specifically, in this embodiment, in order to quantify and mediate a user's engagement, a linear regression-based algorithm is used that predicts a user's time spent (TS) on each program aspect of a digital therapeutic (DTx) based on trends in that user's behavior and the time of day (TOD).

The algorithm is trained on a user-to-user basis, which allows for the minimization of predictors considered and predictions made solely on that user's behavior. After predicting a user's TS, the algorithm detects whether the user's actual TS deviated above or below the predicted value for the user when interacting with a program aspect. When deviations occur, users receive feedback in order to promote adherence and continued engagement with their treatment.

First, data is collected from a user for the initial predetermined period of time (such as one month) of their treatment using the existing DTx data platform in order to train and test the predictive model. The platform collects demographic and activity data from the user. Specifically, the platform collects time stamps of when a user interacts with a program aspect. DTx programs contain 2 types of program aspects that may be used for treatment:
1. Missions, which are activities that mainly contain text and include some sections that require user interaction; and
2. Features, which are activities that mainly contain sections that require user interaction and include some text.

Missions and features can differ on a mission-to-mission or a feature-to-feature basis, depending on the treatment and the specific DTx. For example, some features can range from requiring only one input from the user (e.g., a user logging their mood) to requiring a user's attention and participation for a set period of time (e.g., a 5-minute long breathing exercise). There are also typically no restrictions on how much a user can use a feature.

Some missions can range from including several sentences of information and no user interaction (e.g., a user learns about their treatment and how a DTx can benefit them) to being based only on receiving user input (i.e., a user selects goals from a list and saving them). Missions also typically cannot be revisited by a user once completed. Because of the above, time stamp data is split into groups based on the following:
1. Features that could be repeatedly accessed by a user are individually considered; and
2. Missions are considered in 2 groups—short missions (SMs) (a predetermined number of words (such as 200) or less) and long missions (LMs) (over a predetermined number of words (such as over 200)). The word count threshold for distinguishing between SMs and LMs can be determined by performing a regression analysis in which time spent (TS) on a mission is predicted. The threshold would be selected based on the largest change in TS. For example, if 0 to 99 words TS averages 30 seconds, 100 to 199 words TS averages at 45 seconds, 200 to 299 words average 70 seconds, and 300 to 399 averages 90 seconds, 200 words would be chosen as the threshold as the change in TS is 25 seconds.

Splitting data in this way allows for predictions made on features to be based on collected data of the user's interaction with that feature and predictions made on missions to be based on collected data of the user's interaction with missions of similar length, as missions could not be revisited (and thus would not be repeated).

Time spent (TS) on a program aspect (feature or mission type), a, is defined as the change in time (Equation 6):

$$TS_a = t_2 - t_1$$

In Equation 6, shown above, $t_2$ is the time stamp of when a user begins using a program aspect and $t_1$ is the preceding time stamp of when a user begins using a different program aspect. In situations where a user first opened the app, their TS would be calculated by (Equation 7):

$$TS_a = t_2 - t_0$$

In Equation 7, shown above, $t_2$ is the time stamp of when a user begins using a program aspect and to is the time stamp of when a user first opens the DTx. For example, if a user logged their mood at 5:30 PM, began Mission 1 (LM) at 5:32 PM, which they then finished at 5:40 PM, their calculated TS value for the log mission feature would be 2 minutes (5:32 PM minus 5:30 PM) and their calculated TS value for a LM would be 8 minutes (5:40 PM minus 5:32 PM).

As time stamp and TS data is collected and calculated on an individual user basis, time of day (TOD) is considered the main predictor in the algorithm as other factors that might impact overall user interaction with a mobile application or smartphone (demographics, physical disabilities, etc.) would be constant for that particular user. Furthermore, it is assumed that there is a linear relationship between time spent on a program aspect and TOD for each user (e.g., the later/earlier in the day a user interacts with a program aspect, the larger/smaller the TS value). This leads to further parsing of the training data into 3 groups for a program aspect:
1. $TS_{a,M}$ (TS of a (program aspect) in the morning between the hours of, for example, 5 AM to 11:59 AM inclusive),
2. $TS_{a,A}$ (TS of a (program aspect) in the afternoon between the hours, for example, of 12 PM to 5:59 PM inclusive),
3. $TS_{a,E}$ (TS of a (program aspect) in the evening between the hours, for example, of 6 PM to 4:59 AM inclusive)

In total, the total number of groups in a training data set for a DTx would be determined by (Equation 8):

$$\#of\ Groups = (2+f)*3$$

In Equation 8, shown above, f is the total number of program aspects (Missions and Features) in the DTx, all missions in the DTx are split into the 2 mission type groups (SM and LM) and each group is then split in 3 groups. For example, if a DTx had 5 missions (3 SMs+2 LMs) and 3 features, the training data set would have a total of 15 groups: 1. $TS_{SM,M}$, 2. $TS_{SM,A}$, 3. $TS_{SM,E}$, 4. $TS_{LM,M}$, 5. $TS_{LM,A}$, 6. $TS_{LM,E}$, 7. $TS_{F1,M}$, 8. $TS_{F1,A}$, 9. $TS_{F1,E}$, 10. $TS_{F2,M}$, 11. $TS_{F2,A}$, 12. $TS_{F2,E}$, 13. $TS_{F3,M}$, 14. $TS_{F3,A}$, 15. $TS_{F3,E}$.

As noted above, a linear regression-based algorithm may be used to quantify and mediate a user's engagement. A linear regression assumes that there is linear relationship between an output and a set of determined input values. The influence a specific input value has on an output is determined by its weight, represented by model coefficients. A linear regression can be represented as (Equation 9):

$$y=\theta_0+\theta_1 x_1+\theta_2 x_2+ \ldots +\theta_n x_n$$

In Equation 9, shown above, y is the predicted response, θ are model coefficients (learned during algorithm training/ model fitting), $\theta_0$ is the intercept, $x_1$ is the first predictor, $\theta_1$ is the coefficient for $x_1$, $x_n$ is the nth predictor, and $\theta_n$ is the predictor for $x_n$. As it is assumed that other predictors are represented in the calculated TS values used to train the model and the main predictor for our model is TOD, the equation for our model would be represented as (Equation 10):

$$TS_{a,TOD}=\theta_0+\theta_1 x_1$$

In Equation 10, shown above, $TS_a$ is the predicted TS value for a, a program aspect at a TOD, $\theta_0$ is the intercept, $x_i$ is the TOD, and $\theta_1$ is the coefficient for $x_1$. The intercept is the value at which the predictor is zero. The value itself may not be significant to the model but must be considered in order to minimize any biases that are not accounted for by the predictor. If the value is not considered, it is assumed to be zero. On a 2D plane, this forces the equation to go through the origin, skewing the predicted values and lowering the accuracy of the model. The coefficient $\theta_1$ represents the weight of the TOD. The higher the coefficient, the more TOD will affect $TS_a$. As predictions are made for each program aspect in a DTx, the number of models trained in the algorithm are dependent on the number of groups being considered. For example, if a DTx had 5 missions (3 SMs and 2 LMs) and 3 features, 15 models would be trained in order to predict TS values for a user for each.

When a user interacts with a program aspect (feature, SM, or LM), a TS prediction is made. Comparisons between the predicted value and real-time calculated TS values are then made by the algorithm. Deviations from the predicted value are recorded for the user. After three deviations are recorded for a user, the user receives a message randomly selected from a library containing (1) alerts that warn them of their behavior; (2) information on the importance of adhering to their treatment, and (3) humorous messages. Some of the content in these messages may be customized to the deviation behavior shown by the user. For example, if a user is completing a program aspect too quickly (than predicted TS), he or she may receive a message about not completing the program aspect carefully enough. The type of message shown is recorded (alert, information, or humor). If three more deviations occur within the span of 7 days, the user receives a message that is randomly selected from the other two types of messages. This is done to determine a feedback method that would effectively promote user engagement on an individual basis.

FIGS. 3A-3J show source code that can implement one or more aspects of an embodiment of the present invention. In particular, the algorithms shown in FIGS. 3A-3J show a novel pop-up prompt interface designed to engage the user and increase the user's engagement with a mobile application such as one prescribed or recommended by a clinician (e.g., an application designed for smoking cessation). The prompt is a pop-up mini-screen that appears at scheduled times on a user's device such as a smartphone to remind the user to maintain his medical, psychological, and/or behavioral treatment routine.

Various programming languages may be used to implement embodiments of the present invention including Ionic+ Python+Angular. Ionic is an open source, cross-platform framework used to develop hybrid mobile applications. Ionic is a mobile app development framework based on the HTML5 programming language.

Various databases may be used in embodiments of the present invention including MongoDB, which is a cross-platform document-oriented database program. Classified as a NoSQL database program, MongoDB uses JSON-like documents with optional schemas.

AWS+Elastic Beanstalk+Docker may also be used. AWS Elastic Beanstalk is an easy-to-use service for deploying and scaling web applications and services developed with Node.js and Docker on servers such as Apache, Nginx.

Elastic Beanstalk automatically handles the deployment, from capacity provisioning, load balancing, auto-scaling to application health monitoring.

The algorithms shown in FIGS. 3A-3J are as follows.

The first algorithm includes a prompt application configured to iteratively change attributes of each subsequent prompt, which may include the following "Attribute Categories": (1) font coloration, (2) background colors, (3) border colors, (4) font, (5) font size, (6) prompt shapes, (7) prompt movements (prompt flying from top, prompt flying from bottom, prompt flying in from left, prompt flying in from right, prompt appearing, broken up prompt coming together to fall a single prompt, etc.), (8) prompt opacity/ transparency, (9) accompanying sounds or tunes, (10) accompanying images, (11) positions of the "Action Buttons", as will be described below, (12) shapes of the "Action Buttons", (13) font size of the Action Buttons, (14) font color of the Action Buttons, (15) background color of the Action Buttons, (16) font of the Action Buttons. Other categories may also be included as Attribute Categories. Instantiations of the Attribute Categories refer to the possible changes within an Attribute Category. Instantiations for font coloration include red, blue, yellow, orange, purple, green, black, green, white, and the like; instantiations for prompt shapes include square, rectangle, circle, oval, triangle, and the like; instantiations for prompt movements include horizontal movement, vertical movement, circular movement, random walk, and the like; instantiations for font size include, for example, 9, 10, 11, and 12. The instantiations may be determined randomly. For example, if a use selects an action button representing the font size, the application will randomly select a number from 6-24 of the font size. Thus, the font size of the text in the subsequent popup will be a randomly selected number 6-24.

The second algorithm includes creating an Attribute Database to store the possible instantiations for each Attribute Category.

In the third algorithm, the prompt displays text ("Prompt Text") called from a Text Database, and the prompt may be closed after (1) a designated period of time to ensure that the user has read the text, and/or (2) the user selects one of two Action Buttons, which appear on the prompt only after the designated period of time.

In the fourth algorithm, each of the Action Buttons identify a change in the instantiation of a different Attribute Category. For example, a first Action Button may result in a change of the prompt shape to an oval while the second Action Button may result in a change of the accompanying sound to "Twinkle, Twinkle, Little Star."

In the fifth algorithm, the language present for each Action Button ("Action Button Language") corresponds to a set of multiple instantiations within a given Attribute Category, one of which will be selected randomly, so that the user will not know exactly what the instantiation will be, although the instantiation is suggested by the language of the Action Button. For example, if an Action Button reads "See Something Funny," an image will be randomly selected from a set that includes, for example, a baby eating a puppy's food while the puppy watches sadly, a man jumping out of a window only to be caught by a bird, and many other options.

Figure 4:
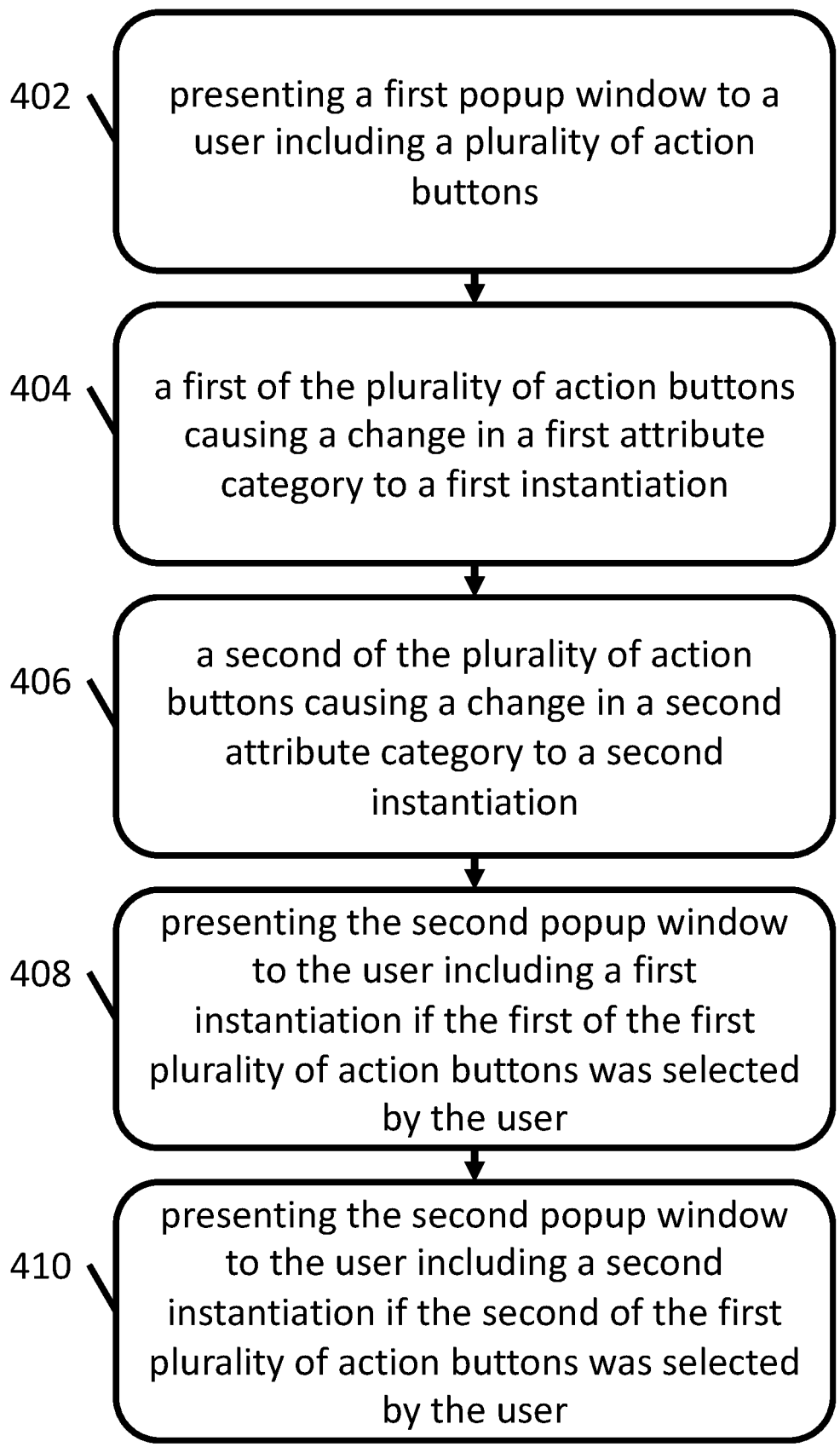
FIG. 4 illustrates a flowchart of one or more aspects of an embodiment of the present invention.

FIG. 4 illustrates a flowchart of one or more aspects of an embodiment of the present invention. Provided may be a method for increasing mobile application user engagement in a remote digital therapeutic computing environment, the method comprising, step 402, presenting a first popup window to a user including a plurality of action buttons, step 404, a first of the plurality of action buttons causing a change in a first attribute category to a first instantiation, and, step 406, a second of the plurality of action buttons causing a change in a second attribute category to a second instantiation, the first attribute category and the second attribute category comprising a type of attribute category of a second popup window; and, step 408, subsequent to the presenting the first popup window to the user, presenting the second popup window to the user including a first instantiation if the first of the first plurality of action buttons was selected by the user, and, step 410, a second instantiation if the second of the first plurality of action buttons was selected by the user, wherein the first and second instantiations are presented according to a digital therapeutic program.

While this invention has been described in conjunction with the embodiments outlined above, many alternatives, modifications and variations will be apparent to those skilled in the art upon reading the foregoing disclosure. Accordingly, the embodiments of the invention, as set forth above, are intended to be illustrative, not limiting. Various changes may be made without departing from the spirit and scope of the invention.

PRIORITY

The present application claims priority to U.S. Provisional Patent Application No. 62/955,011, which was filed in the United States Patent and Trademark Office on Dec. 30, 2019, the entire disclosure of which is incorporated herein by reference.

INTRODUCTION

Embodiments of the invention relate generally to an apparatus for determining whether users of software are actively engaged and interacting with a software application. Such software may include applications that may be running on an electronic device including a smartphone, tablet, or the like.

Some users may be using certain software, for example, apps on a smartphone, tablet, or other device, without due care and/or adequate engagement.

For example, users of apps or other software may not be carefully reading the prompts, not be carefully selecting their responses, not be paying attention to any images or storyline that may appear on their screens, not be responding to prompts or questions in a timely manner, responding to such prompts or questions too quickly, responding to prompts or questions without carefully reading them, and the like.

However, it may be particularly important that users are engaged, especially when use of such software is recommended and/or prescribed by a medical professional and/or other clinician for the diagnosis or treatment of certain conditions such as insomnia or smoking cessation.

It would be desirable, therefore, to provide apparatuses, systems and methods for determining whether users of certain software are actively engaged and interacting with a software application as directed by their medical professional and/or clinician.

BRIEF DESCRIPTION OF THE DRAWINGS

FIG. 1 illustrates a block diagram of a distributed computer system that can implement one or more aspects of an embodiment of the present invention;

FIG. 2 illustrates a block diagram of an electronic device that can implement one or more aspects of an embodiment of the invention;

FIGS. 3A-3J show source code that can implement one or more aspects of an embodiment of the present invention;

FIG. 4 illustrates a flowchart of one or more aspects of an embodiment of the present invention; and FIG. 5 illustrates an example of a regression tree as contemplated by one or more embodiments of the present invention.

While the invention is described with reference to the above drawings, the drawings are intended to be illustrative, and the invention contemplates other embodiments within the spirit of the invention.

DETAILED DESCRIPTION

The present invention will now be described more fully hereinafter with reference to the accompanying drawings which show, by way of illustration, specific embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as devices or methods. Accordingly, the present invention may take the form of an entirely hardware embodiment, an entirely software embodiment, or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrases "in one embodiment," "in an embodiment," and the like, as used herein, does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" includes plural references. The meaning of "in" includes "in" and "on."

It is noted that description herein is not intended as an extensive overview, and as such, concepts may be simplified in the interests of clarity and brevity.

All documents mentioned in this application are hereby incorporated by reference in their entirety. Any process described in this application may be performed in any order and may omit any of the steps in the process. Processes may also be combined with other processes or steps of other processes.

FIG. 1 illustrates components of one embodiment of an environment in which the invention may be practiced. Not all of the components may be required to practice the invention, and variations in the arrangement and type of the components may be made without departing from the spirit or scope of the invention. As shown, the system 100 includes one or more Local Area Networks ("LANs")/Wide Area Networks ("WANs") 112, one or more wireless networks 110, one or more wired or wireless client devices 106, mobile or other wireless client devices 102-105, servers 107-109, and may include or communicate with one or more data stores or databases. Various of the client devices 102-106 may include, for example, desktop computers, laptop computers, set top boxes, tablets, cell phones, smart phones, smart speakers, wearable devices (such as the Apple Watch) and the like. Servers 107-109 can include, for example, one or more application servers, content servers, search servers, and the like. FIG. 1 also illustrates application hosting server 113.

FIG. 2 illustrates a block diagram of an electronic device 200 that can implement one or more aspects of an apparatus, system and method for increasing mobile application user engagement (the "Engine") according to one embodiment of the invention. Instances of the electronic device 200 may include servers, e.g., servers 107-109, and client devices, e.g., client devices 102-106. In general, the electronic device 200 can include a processor/CPU 202, memory 230, a power supply 206, and input/output (I/O) components/devices 240, e.g., microphones, speakers, displays, touchscreens, keyboards, mice, keypads, microscopes, GPS components, cameras, heart rate sensors, light sensors, accelerometers, targeted biometric sensors, etc., which may be operable, for example, to provide graphical user interfaces or text user interfaces.

A user may provide input via a touchscreen of an electronic device 200. A touchscreen may determine whether a user is providing input by, for example, determining whether the user is touching the touchscreen with a part of the user's body such as his or her fingers. The electronic device 200 can also include a communications bus 204 that connects the aforementioned elements of the electronic device 200. Network interfaces 214 can include a receiver and a transmitter (or transceiver), and one or more antennas for wireless communications.

The processor 202 can include one or more of any type of processing device, e.g., a Central Processing Unit (CPU), and a Graphics Processing Unit (GPU). Also, for example, the processor can be central processing logic, or other logic, may include hardware, firmware, software, or combinations thereof, to perform one or more functions or actions, or to cause one or more functions or actions from one or more other components. Also, based on a desired application or need, central processing logic, or other logic, may include, for example, a software-controlled microprocessor, discrete logic, e.g., an Application Specific Integrated Circuit (ASIC), a programmable/programmed logic device, memory device containing instructions, etc., or combinatorial logic embodied in hardware. Furthermore, logic may also be fully embodied as software.

The memory 230, which can include Random Access Memory (RAM) 212 and Read Only Memory (ROM) 232, can be enabled by one or more of any type of memory device, e.g., a primary (directly accessible by the CPU) or secondary (indirectly accessible by the CPU) storage device (e.g., flash memory, magnetic disk, optical disk, and the like). The RAM can include an operating system 221, data storage 224, which may include one or more databases, and programs and/or applications 222, which can include, for example, software aspects of the program 223. The ROM 232 can also include Basic Input/Output System (BIOS) 220 of the electronic device.

Software aspects of the program 223 are intended to broadly include or represent all programming, applications, algorithms, models, software and other tools necessary to implement or facilitate methods and systems according to embodiments of the invention. The elements may exist on a single computer or be distributed among multiple computers, servers, devices or entities.

The power supply 206 contains one or more power components, and facilitates supply and management of power to the electronic device 200.

The input/output components, including Input/Output (I/O) interfaces 240, can include, for example, any interfaces for facilitating communication between any components of the electronic device 200, components of external devices (e.g., components of other devices of the network or system 100), and end users. For example, such components can include a network card that may be an integration of a receiver, a transmitter, a transceiver, and one or more input/output interfaces. A network card, for example, can facilitate wired or wireless communication with other devices of a network. In cases of wireless communication, an antenna can facilitate such communication. Also, some of the input/output interfaces 240 and the bus 204 can facilitate communication between components of the electronic device 200, and in an example can ease processing performed by the processor 202.

Where the electronic device 200 is a server, it can include a computing device that can be capable of sending or receiving signals, e.g., via a wired or wireless network, or may be capable of processing or storing signals, e.g., in memory as physical memory states. The server may be an application server that includes a configuration to provide one or more applications, e.g., aspects of the Engine, via a network to another device. Also, an application server may, for example, host a web site that can provide a user interface for administration of example aspects of the Engine.

Any computing device capable of sending, receiving, and processing data over a wired and/or a wireless network may act as a server, such as in facilitating aspects of implementations of the Engine. Thus, devices acting as a server may include devices such as dedicated rack-mounted servers, desktop computers, laptop computers, set top boxes, integrated devices combining one or more of the preceding devices, and the like.

Servers may vary widely in configuration and capabilities, but they generally include one or more central processing units, memory, mass data storage, a power supply, wired or wireless network interfaces, input/output interfaces, and an operating system such as Windows Server, Mac OS X, Unix, Linux, FreeBSD, and the like.

A server may include, for example, a device that is configured, or includes a configuration, to provide data or content via one or more networks to another device, such as in facilitating aspects of an example apparatus, system and method of the Engine. One or more servers may, for example, be used in hosting a Web site, such as the web site www.microsoft.com. One or more servers may host a variety of sites, such as, for example, business sites, informational sites, social networking sites, educational sites, wikis, financial sites, government sites, personal sites, and the like.

Servers may also, for example, provide a variety of services, such as Web services, third-party services, audio services, video services, email services, HTTP or HTTPS services, Instant Messaging (IM) services, Short Message Service (SMS) services, Multimedia Messaging Service (MMS) services, File Transfer Protocol (FTP) services, Voice Over IP (VOIP) services, calendaring services, phone services, and the like, all of which may work in conjunction with example aspects of an example systems and methods for the apparatus, system and method embodying the Engine. Content may include, for example, text, images, audio, video, and the like.

In example aspects of the apparatus, system and method embodying the Engine, client devices may include, for example, any computing device capable of sending and receiving data over a wired and/or a wireless network. Such client devices may include desktop computers as well as portable devices such as cellular telephones, smart phones, display pagers, Radio Frequency (RF) devices, Infrared (IR) devices, Personal Digital Assistants (PDAs), handheld computers, GPS-enabled devices tablet computers, sensor-equipped devices, laptop computers, set top boxes, wearable computers such as the Apple Watch and Fitbit, integrated devices combining one or more of the preceding devices, and the like.

Client devices such as client devices 102-106, as may be used in an example apparatus, system and method embodying the Engine, may range widely in terms of capabilities and features. For example, a cell phone, smart phone or tablet may have a numeric keypad and a few lines of monochrome Liquid-Crystal Display (LCD) display on which only text may be displayed. In another example, a Web-enabled client device may have a physical or virtual keyboard, data storage (such as flash memory or SD cards), accelerometers, gyroscopes, respiration sensors, body movement sensors, proximity sensors, motion sensors, ambient light sensors, moisture sensors, temperature sensors, compass, barometer, fingerprint sensor, face identification sensor using the camera, pulse sensors, heart rate variability (HRV) sensors, beats per minute (BPM) heart rate sensors, microphones (sound sensors), speakers, GPS or other location-aware capability, and a 2D or 3D touch-sensitive color screen on which both text and graphics may be displayed. In some embodiments multiple client devices may be used to collect a combination of data. For example, a smart phone may be used to collect movement data via an accelerometer and/or gyroscope and a smart watch (such as the Apple Watch) may be used to collect heart rate data. The multiple client devices (such as a smart phone and a smart watch) may be communicatively coupled.

Client devices, such as client devices 102-106, for example, as may be used in an example apparatus, system and method implementing the Engine, may run a variety of operating systems, including personal computer operating systems such as Windows, iOS or Linux, and mobile operating systems such as iOS, Android, Windows Mobile, and the like. Client devices may be used to run one or more applications that are configured to send or receive data from another computing device. Client applications may provide and receive textual content, multimedia information, and the like. Client applications may perform actions such as browsing webpages, using a web search engine, interacting with various apps stored on a smart phone, sending and receiving messages via email, SMS, or MMS, playing games (such as fantasy sports leagues), receiving advertising, watching locally stored or streamed video, or participating in social networks.

In example aspects of the apparatus, system and method implementing the Engine, one or more networks, such as networks 110 or 112, for example, may couple servers and client devices with other computing devices, including through wireless network to client devices. A network may be enabled to employ any form of computer readable media for communicating information from one electronic device to another. The computer readable media may be non-transitory. A network may include the Internet in addition to Local Area Networks (LANs), Wide Area Networks (WANs), direct connections, such as through a Universal Serial Bus (USB) port, other forms of computer-readable media (computer-readable memories), or any combination thereof. On an interconnected set of LANs, including those based on differing architectures and protocols, a router acts as a link between LANs, enabling data to be sent from one to another.

Communication links within LANs may include twisted wire pair or coaxial cable, while communication links between networks may utilize analog telephone lines, cable lines, optical lines, full or fractional dedicated digital lines including T1, T2, T3, and T4, Integrated Services Digital Networks (ISDNs), Digital Subscriber Lines (DSLs), wireless links including satellite links, optic fiber links, or other communications links known to those skilled in the art. Furthermore, remote computers and other related electronic devices could be remotely connected to either LANs or WANs via a modem and a telephone link.

A wireless network, such as wireless network 110, as in an example apparatus, system and method implementing the Engine, may couple devices with a network. A wireless network may employ stand-alone ad-hoc networks, mesh networks, Wireless LAN (WLAN) networks, cellular networks, and the like.

A wireless network may further include an autonomous system of terminals, gateways, routers, or the like connected by wireless radio links, or the like. These connectors may be configured to move freely and randomly and organize themselves arbitrarily, such that the topology of wireless network may change rapidly. A wireless network may further employ a plurality of access technologies including 2nd (2G), 3rd (3G), 4th (4G) generation, Long Term Evolution (LTE) radio access for cellular systems, WLAN, Wireless Router (WR) mesh, and the like. Access technologies such as 2G, 2.5G, 3G, 4G, and future access networks may enable wide area coverage for client devices, such as client devices with various degrees of mobility. For example, a wireless network may enable a radio connection through a radio network access technology such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, and the like. A wireless network may include virtually any wireless communication mechanism by which information may travel between client devices and another computing device, network, and the like.

Internet Protocol (IP) may be used for transmitting data communication packets over a network of participating digital communication networks, and may include protocols such as TCP/IP, UDP, DECnet, NetBEUI, IPX, Appletalk, and the like. Versions of the Internet Protocol include IPv4 and IPv6. The Internet includes local area networks (LANs), Wide Area Networks (WANs), wireless networks, and long-haul public networks that may allow packets to be communicated between the local area networks. The packets may be transmitted between nodes in the network to sites each of which has a unique local network address. A data communication packet may be sent through the Internet from a user site via an access node connected to the Internet. The packet may be forwarded through the network nodes to any target site connected to the network provided that the site address of the target site is included in a header of the packet. Each packet communicated over the Internet may be routed via a path determined by gateways and servers that switch the packet according to the target address and the availability of a network path to connect to the target site.

The header of the packet may include, for example, the source port (16 bits), destination port (16 bits), sequence number (32 bits), acknowledgement number (32 bits), data offset (4 bits), reserved (6 bits), checksum (16 bits), urgent pointer (16 bits), options (variable number of bits in multiple of 8 bits in length), padding (may be composed of all zeros and includes a number of bits such that the header ends on a 32 bit boundary). The number of bits for each of the above may also be higher or lower.

A "content delivery network" or "content distribution network" (CDN), as may be used in an example apparatus, system and method implementing the Engine, generally refers to a distributed computer system that comprises a collection of autonomous computers linked by a network or networks, together with the software, systems, protocols and techniques designed to facilitate various services, such as the storage, caching, or transmission of content, streaming media and applications on behalf of content providers. Such services may make use of ancillary technologies including, but not limited to, "cloud computing," distributed storage, DNS request handling, provisioning, data monitoring and reporting, content targeting, personalization, and business intelligence. A CDN may also enable an entity to operate and/or manage a third party's web site infrastructure, in whole or in part, on the third party's behalf.

A Peer-to-Peer (or P2P) computer network relies primarily on the computing power and bandwidth of the participants in the network rather than concentrating it in a given set of dedicated servers. P2P networks are typically used for connecting nodes via largely ad hoc connections. A pure peer-to-peer network does not have a notion of clients or servers, but only equal peer nodes that simultaneously function as both "clients" and "servers" to the other nodes on the network.

Embodiments of the present invention include apparatuses, systems, and methods implementing the Engine. Embodiments of the present invention may be implemented on one or more of client devices 102-106, which are communicatively coupled to servers including servers 107-109. Moreover, client devices 102-106 may be communicatively (wirelessly or wired) coupled to one another. In particular, software aspects of the Engine may be implemented in the program 223. The program 223 may be implemented on one or more client devices 102-106, one or more servers 107-109, and 113, or a combination of one or more client devices 102-106, and one or more servers 107-109 and 113.

Embodiments of the present invention, which may be implemented at least in part in the program 223, relate to apparatuses, systems and methods for increasing mobile application user engagement.

Disclosed herein are apparatuses, systems and methods for determining whether users of software are actively engaged and interacting with a software application.

Pharmaceuticals are most likely to provide beneficial results when taken as prescribed, and patient compliance/adherence to medical treatment as prescribed by a clinician is an established problem in both clinical trials and the real world.

Another form of treatment in which patient compliance/adherence is important is one that consists of or includes interaction with an electronic device such as a smartphone, tablet, laptop, or the like (i.e., Digital Therapeutics (DTx)). Such treatment may be complementary to or may replace a pharmaceutical treatment. For example, if a patient is addicted to smoking, a clinician may prescribe a treatment of interacting with software running on an electronic device that monitors smoking by the patient or otherwise interacts with the patient regarding smoking.

For example, the software may determine the location of the user by using location services (such as a GPS receiver and associated software) of the electronic device. If the software determines that the user is in a location where the user, and/or the population as a whole, and/or the user's demographic, is more likely to smoke, the software may take certain actions such as activating a camera, activating a microphone, activating sensors that can determine the presence of smoke, reminding the user not to smoke by generating a message on the screen of the electronic device, asking the user if he or she is smoking by generating a message on the screen of the digital device (including an answer prompt), calling the user with a prerecorded message, and the like.

However, a person that has been prescribed such treatment may simply "click through" any prompts and would thus not provide positive results. Moreover, simply clicking through or not being actively engaged would not provide accurate results as to the treatment's efficacy. For example, a user can easily click through an activity answering "yes" or "done" to activities that were never actually completed by the user (prompts not actually read by the user, tasks not performed by the user, and the like).

Embodiments of the present invention measure adherence of a given treatment by, for example, measuring the user's click speed as they navigate through the modules of the application. To bridge the gap between adherence and engagement, embodiments of the present invention include algorithms to personalize compliance remediation techniques based on user demographics, click speed, and baseline user habits.

To summarize, according to certain embodiments of the present invention, when a user begins clicking faster or slower than certain pre-defined thresholds, alerts and messages will appear in the app in order to: (1) attract the user's attention; (2) alert the user that the software is monitoring their behavior since users are generally more compliant when they believe they are being monitored; and (3) encourage the user to modify their behavior to engage more actively with the software. This results in a more compliant user and more successful treatment.

More specifically, once a user is prescribed the treatment (i.e., interaction with a DTx, a software/app running on an electronic device such as a smartphone), the user will first input basic demographic information (e.g., age, weight, location, health history, and the like). During the first two (2) (or 1 or 3 or 4) weeks of treatment, baseline user habits are first recorded by the software. These inputs will then be used to monitor threshold limits throughout the treatment. If a threshold is passed (e.g., user click speed is above or below a defined personal limit of that user), the software will deploy in-app alerts and messages to encourage the user to be more engaged with the product.

The in-app alerts and messages will be accessed from a library/database of messages, alerts, and educational information, stored either on the electronic device or on another device such as a server communicatively coupled with the electronic device. User response to the app (i.e., determining whether alerts were effective and whether the user is more or less engaged) is assessed by the software, and similar types of alerts will be used on an ongoing basis to promote user treatment engagement if the app determines that the thresholds have been passed. $\theta_n$ the other hand, if the software determines that alerts were ineffective, different alerts will be selected from the library/database to determine whether other alerts may be more effective at changing user behavior.

The following provides further detail regarding the software for determining whether users of software are actively engaged and interacting with a software application.

To quantify a user's engagement, an embodiment of the present invention first creates a user profile based on information collected from demographic questions and calculates baseline Click Speed (CS) values and Deviation Thresholds (DTs) for the user during the initial weeks (e.g., 2) of treatment. The software then detects when the CS, calculated as the user is interacting with the app, deviates above or below the DT. When deviations occur, users receive feedback in order to promote adherence and continued engagement with their treatment.

When a user first begins treatment, the user is asked questions about his or her age and physical disabilities. These factors are considered relevant when creating a baseline for a user as they could impact the speed at which a user interacts with a mobile app. For example, if a user is over 55 years old or has a physical disability that could affect their dexterity (such as brain or spinal cord injuries, cerebral palsy, arthritis, and more), the user may interact with a mobile app slower than an average person. The user's CS within the software is also recorded during this time and for the two weeks of treatment. CS is defined as the change in time according to the following equation (1): $CS=t_{C2}-t_{C1}$ According to the above equation (1), $t_{C2}$ is the time at which a user clicks on a feature (e.g., button, toggle, image, etc.) on a screen within the app and $t_{C1}$ is the time at which the user either first opened that screen (if $t_{C2}$ is the first time the user interacted with the screen since it was opened) or clicked on another feature (button, toggle, image, etc.) within that screen, if the user has already interacted with the screen.

Embodiments of the present invention include 2 types of program aspects that are relevant for treatment: (1) Missions, which are activities that mainly contain text for the user to read and some sections that require user interaction; and (2) Features, which are activities that mainly contain sections that require user interaction and some text. Because of their differences, CS is tracked for these two aspects separately as the speed at which a user interacts with them may differ.

In addition, time of day is also tracked, as users may exhibit differences in CS depending on time of day. For example, users may be more tired at 3 a.m. as opposed to 3 p.m. Thus, it is necessary to track the time of day and compare the user's CS to the baseline CS for that time of day.

These 2 considerations (differences in program aspects and time) lead to the creation of 6 CS baseline values per user: (1) $CS_{MM}$ (CS of interactions with Missions in the morning, or between the hours of 5 AM to 11:59:59 a.m. inclusive); (2) $CS_{MF}$ (CS of interactions with Features in the morning); (3) $CS_{AM}$ (CS of interactions with Missions in the afternoon, or between the hours of 12 p.m. to 5:59:59 p.m. inclusive); (4) $CS_{AF}$ (CS of interactions with Features in the afternoon); (5) $CS_{EM}$ (CS of interactions with Missions in the evening/night, or between the hours of 6 p.m. to 4:59:59 a.m. inclusive); and (6) $CS_{EF}$ (CS of interactions with DTx features in the evening/night). Deviation thresholds (DTs) were set to 5 seconds (faster or slower) per CS baseline as a default (i.e., Equation (2), DT for $CS=CS\pm5$ seconds). However, if users indicated factors that would impact their CS in their user profile, DTs were adjusted using the following equation (3):

$$DT \text{ for } CS=CS\pm(5*(n+0.25)) \text{ seconds}$$

According to the above equation (3), CS is the click speed baseline value and n is the number of factors that could impact click speed that the user indicated in their profile in response to the initial question posed by the software.

For example, consider a user who is 30 years old with no physical disabilities, and has the following CS baseline values: $CS_{MM}$=62 seconds (s), 2; $CS_{MF}$=25 s, 3; $CS_{AM}$=50 s, 4; $CS_{AF}$=18 s, 5; $CS_{EM}$=55 s, 6; and $CS_{EF}$=20 s The DTs for the above would user would thus be as follows: DT for $CS_{MM}$=62±5 s, 2; DT for $CS_{MF}$=25±5 s, 3; DT for $CS_{AM}$=50±5 s, 4; DT for $CS_{AF}$=18±5 s, 5; DT for $CS_{EM}$=55±5 s, 6; DT for $CS_{EF}$=20±5 s.

That is, for example, with respect to $CS_{MM}$, applying equation (2), the result is 62±5 seconds.

However, if we had a user who had the same CS baseline values but was 60 years old and had arthritis (n=2) (i.e., +1 for being 55 years or older and +1 for having arthritis) their DTs would be: DT for $CS_{MM}$=62±11.25 s, 2. DT for $CS_{MF}$=25±11.25 s, 3. DT for $CS_{AM}$=50±11.25 s, 4. DT for $CS_{AF}$=18±11.25 s, 5. DT for $CS_{EM}$=55±11.25 s, 6. DT for $CS_{EF}$=20±11.25 s.

That is, for example, with respect to $CS_{MM}$, applying equation (3), 62±(5*(2+0.25)) s=62±11.25 s.

After the CS baseline values and DTs are calculated, comparisons between CS values are calculated each time the user interacts with the mobile app and DTs for the relevant time-of-day are made. Deviations from DTs are recorded for the user. For example, for the $CS_{MM}$ example for the 60 year old user with arthritis, discussed above, assuming the $CS_{MM}$ was more than 73.25 seconds or less than 50.75 seconds, a deviation would be determined and stored in a database, either on the electronic device or a database residing on a server communicatively coupled to the electronic device.

After a predetermined number (e.g., 3) of deviations are recorded for a user, a determination is made that the user is not properly engaging with the software. The user then receives a message randomly selected from a library containing alerts that warns the user of their behavior, and provides information on the importance of adhering to their treatment and humorous messages.

Some of the content in these messages is customized to the deviation behavior shown by the user (faster/slower clicks). For example, if the CS of the user discussed above is higher than 73.25 seconds, a message tailored for slow click speed is selected from the database. However, if the CS of the user discussed above is lower than 50.75 seconds, a message tailored for fast click speed is selected from the database.

The type of message displayed to the user on the screen of the electronic device is then recorded (e.g., alert, information, or humor).

After the first such message is displayed to the user, the software determines whether there is an ongoing problem of user engagement. If a predetermined number, e.g., 3, of additional deviations occur within the span of the next predetermined number, e.g., 7, of days, the user receives a message randomly selected from the other two types of messages. That is, for example, if the user was originally shown a message selected from the "humor" messages, either an "information" or an "alert" message would then be shown. This is so to attempt to determine a feedback method that would effectively promote user engagement on an individual basis. That is, if a "humor" message was not effective in promoting user engagement, it is then determined whether an "information" or "alert" message is effective.

For example, if the algorithm detects three deviations from a user and sends an information message to the user such as "Medication has best results when taken as prescribed. Likewise, engaging with this digital therapeutic is essential in ensuring you are receiving adequate treatment!" and 4 days later, the software detects another 3 deviations from the user, the user may then receive an alert message such as "You've been completing your missions faster than usual! Make sure you're reading through the missions completely!"

If, after the "alert" message, the user's CS does not deviate from the DTs for the next 7 days, the software would record alert messages as being an effective form of feedback method for promoting engagement. The software would also record that the "information" message is not an effective form of feedback method for promoting engagement. Thus, if the user then again begins to deviate from DTs, they would receive another "alert" message since it has been determined that alert messages are more effective than information messages.

The above embodiments generally relate to using CS to determine whether the user is adequately engaged. However, other factors may be used instead of or in conjunction with user CS.

For example, software running on an electronic device may determine the proportion of the time a user is looking at the relevant portion of the electronic device screen (i.e., eye tracking). For example, some smartphones allow picture-in-picture functionality, where the user may be interacting with one app (e.g., watching a movie or a TV show in the Netflix app) while also interacting with another app (e.g., an app prescribed by a clinician). In this case, although the CS may indicate that the user is actively engaged with the app prescribed by the clinician, the user may in fact have spent a portion of that time engaged with another app. That is, for example, if the app prescribed by the clinician is in a particular portion of the screen (e.g., the upper right quadrant), the app can determine that 80% of the relevant CS time was actually spent looking at the upper left, lower left, and/or lower right quadrants, engaging with another app such as Netflix.

In order to make the above determination, the app accesses a camera on the electronic device or another camera near the user, which takes one or more photographs or videos of the user, determines the location of the sclera, iris, pupil and other parts of one or both of the eyes of the user. The software takes regular photographs (for example, every 1 second or 0.5 seconds) and determines the point on the screen of the electronic device at which one or both eyes are focused. Once the point on the screen is determined, the software uses certain Application Programming Interfaces (APIs) provided by the electronic device to determine the app the user is focused on. The software then calculates the proportion of points the user was focused on that are on the clinician prescribed app. If the proportion of points is below a certain threshold (e.g., 75%), a determination is made that the user is not engaging with the clinician prescribed app.

In another embodiment, the software running on the electronic device may take multiple photos to determine whether the user is in motion. For example, the software may determine that the user is running or engaged in another activity during which the user would be unlikely to be actively engaged with the clinician prescribed app.

In yet another embodiment, the software running on the electronic device may activate a microphone to determine sounds that may make it unlikely that the user is actively engaged with the clinician prescribed software. For example, when determining user baselines, the app may record the user's voice. The app may then determine, by activating the microphone on the electronic device, whether the user is speaking, other people are speaking, music is playing, the user is attending an event, and the like. If the app determines that the user was speaking more than a certain proportion of the time, the app would determine a deviation.

In yet another embodiment, a machine learning-based algorithm may be used to quantify a user's engagement with a certain app running on an electronic device such a smartphone (e.g., an app that is or includes a DTx). Specifically, in order to quantify a user's engagement, a regression tree-based algorithm is utilized to predict a user's time spent (TS) on each program aspect of a digital therapeutic (DTx) relying on demographics. The algorithm then detects when a particular user's TS deviates above or below the predicted average time spent (ATS) for the user when interacting with a particular program aspect. When deviations occur, a user receives feedback in order to promote adherence and continued engagement with their treatment. That is, once a particular user's demographic information is known (e.g., age, sex, location), a predicted ATS, relying on data from past interactions by other users of the same and/or similar demographics, is generated and a predicted ATS is determined for that user. That predicted ATS is then compared to the user's actual ATS (or TS) when interacting with various features of the DTx. If the predicted ATS is substantially different than the actual ATS (or TS), the DTx may determine that a user is not properly engaging with the DTx or particular aspects thereof. For example, if the actual ATS is substantially longer than the predicted ATS for a particular aspect, the user may have stopped interacting with the particular aspect of the DTx for a certain period of time (e.g., while watching television, using another app, speaking to someone, and the like). In the alternative, if the actual ATS is substantially shorter than the predicted ATS for a particular feature, the user may have interacted with the particular aspect of the DTx without actively engaging with such aspect (e.g., the user may not have been reading the prompts and/or following directions provided by the aspect and was simply "clicking through" to give the illusion that they completed interacting with such feature). A more detailed discussion is provided below.

First, a DTx data platform is utilized in order to develop and train the predictive model. The platform collects data from its users including demographic information provided by users when a profile is first set up (for example, age, sex, and location of a user) and a user's activity and interaction with the DTx. In the alternative, demographic information about a user may be obtained from other sources such as information obtained from publicly available databases, background checks, medical data, finding and crawling a user's social media accounts, and the like. For example, in crawling a user's social media accounts, certain proxies may be used to determine a user's demographic information. For example, if a user uses particular words in their social media posts that are more likely to be used by a certain age demographic (e.g., millennials), it may be assumed such a user's age is that of a millennial (e.g., an average millennial age may be assumed). Similarly, if a user "likes" or comments on a particular musical band, that a particular demographic (such as age) is more likely to listen to, it may be assumed that that user is part of that demographic. As another example, if a user likes or comments about a cause that is more likely to be supported by a particular demographic (such as a particular sex), it may be assumed that that user is part of that demographic.

Once a user's demographics are obtained and stored, time stamps of when a particular user first begins using a program aspect are collected and stored in a database (the database may be stored on the electronic device, such as a smartphone, or on a server communicatively coupled to the electronic device). Also, time stamps of when a particular user stops begins using a program aspect are collected and stored in a database.

As noted above, DTx programs may include 2 types of program aspects that are relevant for treatment: (1) Missions, which are activities that mainly contain text, and some sections that require user interaction; and (2) Features, which are activities that mainly contain sections that require user interaction, and some text. Missions and Features can also differ on a Mission-to-Mission or Feature-to-Feature basis, depending on the treatment and the specific DTx. For example, some missions may range from including several sentences of information and no user interaction (e.g., a mission may include a user learning about their treatment and how a DTx can benefit them, with little to no user interaction) to being based only on receiving user input (e.g., a user selecting goals from a list and saving them). Some Features can range from requiring only one input from the user (i.e., user inputs their mood into the app (e.g., happy, sad, anxious, excited, and the like) to requiring a user's attention and participation for a set period of time (e.g., asking the user to participate in a physical activity such as a 5-minute long breathing exercise). Because of this, time stamp data is extracted and analyzed from an individual program aspect basis. From the time stamp data, time spent (TS) on a program aspect, n, was defined as the change in time (Equation 4):

$$TS_n = t_2 - t_1$$

In Equation 4, shown above, $t_2$ is the time stamp of when a user begins using a program aspect and $t_1$ is the preceding time stamp of when a user begins using a different program aspect, not accounting for idle time (i.e, when application is not in active use). In situations where a user first opened the app, their TS would be calculated by (Equation 5):

$$TS_n = t_2 - t_0$$

In Equation 5, shown above, $t_2$ is the time stamp of when a user begins using a program aspect and to is the time stamp of when a user first opens the DTx. For example, if a user logged their mood using the DTx at 5:30 p.m., began Mission 1 at 5:32 p.m., which they then finished at 5:40 p.m., their TS for the log mission feature would be 2 minutes and their TS for Mission 1 would be 8 minutes. That is, to calculate the TS for Mission 1, using Equation 4, $TS_n = t_2 - t_1$, $t_2$ would be equal to 5:40 p.m., $t_1$, would be equal to 5:32 p.m., thus, $TS_n$ for Mission 1 would be 8 minutes.

Regression trees (a type of Decision Tree) may be constructed for each predictor. That is, various user demographics that are considered predictors for TSs for each program aspect are collected including age, sex, and location. These predictors are then used to construct regression trees. Regression trees are constructed for each predictor (e.g., age, sex, and location). This allows for the interpretation of the most important predictor thresholds and splits. In each tree, different thresholds are tested for age (e.g., ranging from 18 to over 65 years old age), sex (e.g., female or male) and location (e.g., divided into the 5 regions of the United States: West, Southwest, Northeast, Southeast, and Midwest) and the threshold for each predictor that results in the minimum sum of squared residuals (SSR), deviations from empirical data, is selected as a candidate. When examining one predictor, SSR is given by the following equation:

$$SSR = \Sigma_{i=1}^n (y_i - x_i)^2$$

where $y_i$ is the observed average value of the variable to be predicted and $x_i$ is the predicted value. In other words, SSR quantifies the quality of the predictions. The SSR for each candidate is then compared and the candidate with the lowest SSR becomes the root of the tree model (for example, age>=65 in the regression tree shown in FIG. 5). The rest of the tree is then constructed by comparing the lowest SSR of each predictor. Given a user's age, sex, and location, the algorithm then predicts their TS on a specific program aspect. For example, if the thresholds with the lowest SSR values within the predictor groups were as follows:

1. Age>=65 (SSR=11,465)
2. Sex=Female (SSR=18,345)
3. Location=West (SSR=19,642)

Age>=65 would become the root of the tree as it has the lowest SSR value compared to the other two thresholds. The lowest SSR values from each predictor group is compared to grow the tree. FIG. 5 is an example of a short regression tree for Mission 1, considering all predictors.

Once a regression tree, such as the one in FIG. 5, is generated, it may be used to determine the predicted ATS for a particular user. For example, if the particular user is a 64 year male who lives in the Northeast, the regression tree would be traversed as follows. First, the decision point at the root would be evaluated. In this case, if the user had an age of >=65 the predicted ATS would be 7.0±1.5 minutes. That is, if the user had an age of >=65, the predicted ATS would be between 5.5 and 8.5 minutes, inclusive. However, in our case, since the particular user is 64 years old, the algorithm proceeds to the right to the second decision point.

The second decision point determines whether the sex of the particular user is female and, since the user is not female, the algorithm proceeds to the right to determine whether the particular user lives in the West. Since the user does not live in the West, the result of the tree traversal is 4.1±0.2 minutes, or between 3.9 and 4.3 minutes inclusive. Thus, a 64 year old male who lives in the Northeast would have a predicted ATS of between 3.9 and 4.3 minutes, inclusive. However, if the user was a 64 year old male who lives in the West, the algorithm would operate similarly, except at the last decision point, would evaluate to true and result in 4.3±0.3 minutes, or between 4.0 and 4.6 minutes, inclusive.

After a user's TS for a specific program aspect was predicted, comparisons between the predicted value and calculated TS value are made. Deviations from the predicted value are then recorded for the user. After three deviations are recorded for a user, the user receives a message randomly selected from a library of containing alerts that warn them of their behavior, information on the importance of adhering to their treatment, and humorous messages. Some of the content in these messages would be customized to the deviation behavior shown by the user (faster/slower than the predicted TS). The type of message shown is then recorded (alert, information, or humor). If three (or another predetermined number) more deviations occur within the span of a predetermined number of days (e.g., 7 days), the user receives a message that is randomly selected from one of the other two types of messages. This is done to determine a feedback method that would effectively promote user engagement on an individual basis.

For example, if the algorithm detected three deviations from a user within a predetermined period of time and sent an information message such as: "Medication has best results when taken as prescribed. Likewise, engaging with this digital therapeutic is essential in ensuring you are receiving adequate treatment!" and 4 days later, the algorithm detects another three deviations, the user may receive an alert message such as: "You've been completing your missions faster than usual!Make sure you're reading through the missions completely!" However, if the user's CS does not deviate from the DTs for the next 7 days, the algorithm would record alert messages as being an effective form of feedback method for promoting engagement. If the user then began to deviate from DTs after this time span, they would receive another alert message.

In yet another embodiment, another machine learning-based algorithm may be used to quantify a user's engagement with a certain app running on an electronic device such a smartphone (e.g., an app that is or includes a DTx). Specifically, in this embodiment, in order to quantify and mediate a user's engagement, a linear regression-based algorithm is used that predicts a user's time spent (TS) on each program aspect of a digital therapeutic (DTx) based on trends in that user's behavior and the time of day (TOD).

The algorithm is trained on a user-to-user basis, which allows for the minimization of predictors considered and predictions made solely on that user's behavior. After predicting a user's TS, the algorithm detects whether the user's actual TS deviated above or below the predicted value for the user when interacting with a program aspect. When deviations occur, users receive feedback in order to promote adherence and continued engagement with their treatment.

First, data is collected from a user for the initial predetermined period of time (such as one month) of their treatment using the existing DTx data platform in order to train and test the predictive model. The platform collects demographic and activity data from the user. Specifically, the platform collects time stamps of when a user interacts with a program aspect. DTx programs contain 2 types of program aspects that may be used for treatment:

1. Missions, which are activities that mainly contain text and include some sections that require user interaction; and
2. Features, which are activities that mainly contain sections that require user interaction and include some text.

Missions and features can differ on a mission-to-mission or a feature-to-feature basis, depending on the treatment and the specific DTx. For example, some features can range from requiring only one input from the user (e.g., a user logging their mood) to requiring a user's attention and participation for a set period of time (e.g., a 5-minute long breathing exercise). There are also typically no restrictions on how much a user can use a feature.

Some missions can range from including several sentences of information and no user interaction (e.g., a user learns about their treatment and how a DTx can benefit them) to being based only on receiving user input (i.e., a user selects goals from a list and saving them). Missions also typically cannot be revisited by a user once completed. Because of the above, time stamp data is split into groups based on the following:

1. Features that could be repeatedly accessed by a user are individually considered; and
2. Missions are considered in 2 groups—short missions (SMs) (a predetermined number of words (such as 200) or less) and long missions (LMs) (over a predetermined number of words (such as over 200)). The word count threshold for distinguishing between SMs and LMs can be determined by performing a regression analysis in which time spent (TS) on a mission is predicted. The threshold would be selected based on the largest change in TS. For example, if 0 to 99 words TS averages 30 seconds, 100 to 199 words TS averages at 45 seconds, 200 to 299 words average 70 seconds, and 300 to 399 averages 90 seconds, 200 words would be chosen as the threshold as the change in TS is 25 seconds.

Splitting data in this way allows for predictions made on features to be based on collected data of the user's interaction with that feature and predictions made on missions to be based on collected data of the user's interaction with missions of similar length, as missions could not be revisited (and thus would not be repeated).

Time spent (TS) on a program aspect (feature or mission type), a, is defined as the change in time (Equation 6):

$$TS_a = t_2 - t_1$$

In Equation 6, shown above, $t_2$ is the time stamp of when a user begins using a program aspect and $t_1$ is the preceding time stamp of when a user begins using a different program aspect. In situations where a user first opened the app, their TS would be calculated by (Equation 7):

$$TS_a = t_2 - t_0$$

In Equation 7, shown above, $t_2$ is the time stamp of when a user begins using a program aspect and to is the time stamp of when a user first opens the DTx. For example, if a user logged their mood at 5:30 PM, began Mission 1 (LM) at 5:32 PM, which they then finished at 5:40 PM, their calculated TS value for the log mission feature would be 2 minutes (5:32 PM minus 5:30 PM) and their calculated TS value for a LM would be 8 minutes (5:40 PM minus 5:32 PM).

As time stamp and TS data is collected and calculated on an individual user basis, time of day (TOD) is considered the main predictor in the algorithm as other factors that might impact overall user interaction with a mobile application or smartphone (demographics, physical disabilities, etc.) would be constant for that particular user. Furthermore, it is assumed that there is a linear relationship between time spent on a program aspect and TOD for each user (e.g., the later/earlier in the day a user interacts with a program aspect, the larger/smaller the TS value). This leads to further parsing of the training data into 3 groups for a program aspect:

1. $TS_{a,M}$ (TS of a (program aspect) in the morning between the hours of, for example, 5 AM to 11:59 AM inclusive), 2. $TS_{a,A}$ (TS of a (program aspect) in the afternoon between the hours, for example, of 12 PM to 5:59 PM inclusive),
3. $TS_{a,E}$ (TS of a (program aspect) in the evening between the hours, for example, of 6 PM to 4:59 AM inclusive)

In total, the total number of groups in a training data set for a DTx would be determined by (Equation 8):

$$\text{\#of Groups} = (2+f)*3$$

In Equation 8, shown above, f is the total number of program aspects (Missions and Features) in the DTx, all missions in the DTx are split into the 2 mission type groups (SM and LM) and each group is then split in 3 groups. For example, if a DTx had 5 missions (3 SMs+2 LMs) and 3 features, the training data set would have a total of 15 groups: 1. $TS_{SM,M}$, 2. $TS_{SM,A}$, 3. $TS_{SM,E}$, 4. $TS_{LM,M}$, 5. $TS_{LM,A}$, 6. $TS_{LM,E}$, 7. $TS_{F1,M}$, 8. $TS_{F1,A}$, 9. $TS_{F1,E}$, 10. $TS_{F2,M}$, 11. $TS_{F2,A}$, 12. $TS_{F2,E}$, 13. $TS_{F3,M}$, 14. $TS_{F3,A}$, 15. $TS_{F3,E}$.

As noted above, a linear regression-based algorithm may be used to quantify and mediate a user's engagement. A linear regression assumes that there is linear relationship between an output and a set of determined input values. The influence a specific input value has on an output is determined by its weight, represented by model coefficients. A linear regression can be represented as (Equation 9):

$$y = \theta_0 + \theta_1 x_1 + \theta_2 x_2 + \ldots + \theta_n x_n$$

In Equation 9, shown above, y is the predicted response, $\theta$ are model coefficients (learned during algorithm training/model fitting), $\theta_0$ is the intercept, $x_1$ is the first predictor, $\theta_1$ is the coefficient for $x_1$, $x_n$ is the nth predictor, and $\theta_n$ is the predictor for $x_n$. As it is assumed that other predictors are represented in the calculated TS values used to train the model and the main predictor for our model is TOD, the equation for our model would be represented as (Equation 10):

$$TS_{a,TOD} = \theta_0 + \theta_1 x_1$$

In Equation 10, shown above, $TS_a$ is the predicted TS value for a, a program aspect at a TOD, $\theta_0$ is the intercept, $x_i$ is the TOD, and $\theta_1$ is the coefficient for $x_1$. The intercept is the value at which the predictor is zero. The value itself may not be significant to the model but must be considered in order to minimize any biases that are not accounted for by the predictor. If the value is not considered, it is assumed to be zero. On a 2D plane, this forces the equation to go through the origin, skewing the predicted values and lowering the accuracy of the model. The coefficient $\theta_1$ represents the weight of the TOD. The higher the coefficient, the more TOD will affect $TS_a$. As predictions are made for each program aspect in a DTx, the number of models trained in the algorithm are dependent on the number of groups being considered. For example, if a DTx had 5 missions (3 SMs and 2 LMs) and 3 features, 15 models would be trained in order to predict TS values for a user for each.

When a user interacts with a program aspect (feature, SM, or LM), a TS prediction is made. Comparisons between the predicted value and real-time calculated TS values are then made by the algorithm. Deviations from the predicted value are recorded for the user. After three deviations are recorded for a user, the user receives a message randomly selected from a library containing (1) alerts that warn them of their behavior; (2) information on the importance of adhering to their treatment, and (3) humorous messages. Some of the content in these messages may be customized to the deviation behavior shown by the user. For example, if a user is completing a program aspect too quickly (than predicted TS), he or she may receive a message about not completing the program aspect carefully enough. The type of message shown is recorded (alert, information, or humor). If three more deviations occur within the span of 7 days, the user receives a message that is randomly selected from the other two types of messages. This is done to determine a feedback method that would effectively promote user engagement on an individual basis.

FIGS. 3A-3J show source code that can implement one or more aspects of an embodiment of the present invention. In particular, the algorithms shown in FIGS. 3A-3J show a novel pop-up prompt interface designed to engage the user and increase the user's engagement with a mobile application such as one prescribed or recommended by a clinician (e.g., an application designed for smoking cessation). The prompt is a pop-up mini-screen that appears at scheduled times on a user's device such as a smartphone to remind the user to maintain his medical, psychological, and/or behavioral treatment routine.

Various programming languages may be used to implement embodiments of the present invention including Ionic+Python+Angular. Ionic is an open source, cross-platform framework used to develop hybrid mobile applications. Ionic is a mobile app development framework based on the HTML5 programming language.

Various databases may be used in embodiments of the present invention including MongoDB, which is a cross-platform document-oriented database program. Classified as a NoSQL database program, MongoDB uses JSON-like documents with optional schemas.

AWS+Elastic Beanstalk+Docker may also be used. AWS Elastic Beanstalk is an easy-to-use service for deploying and scaling web applications and services developed with Node.js and Docker on servers such as Apache, Nginx.

Elastic Beanstalk automatically handles the deployment, from capacity provisioning, load balancing, auto-scaling to application health monitoring.

The algorithms shown in FIGS. 3A-3J are as follows.

The first algorithm includes a prompt application configured to iteratively change attributes of each subsequent prompt, which may include the following "Attribute Categories": (1) font coloration, (2) background colors, (3) border colors, (4) font, (5) font size, (6) prompt shapes, (7) prompt movements (prompt flying from top, prompt flying from bottom, prompt flying in from left, prompt flying in from right, prompt appearing, broken up prompt coming together to fall a single prompt, etc.), (8) prompt opacity/transparency, (9) accompanying sounds or tunes, (10) accompanying images, (11) positions of the "Action Buttons", as will be described below, (12) shapes of the "Action Buttons", (13) font size of the Action Buttons, (14) font color of the Action Buttons, (15) background color of the Action Buttons, (16) font of the Action Buttons. Other categories may also be included as Attribute Categories. Instantiations of the Attribute Categories refer to the possible changes within an Attribute Category. Instantiations for font coloration include red, blue, yellow, orange, purple, green, black, green, white, and the like; instantiations for prompt shapes include square, rectangle, circle, oval, triangle, and the like; instantiations for prompt movements include horizontal movement, vertical movement, circular movement, random walk, and the like; instantiations for font size include, for example, 9, 10, 11, and 12. The instantiations may be determined randomly. For example, if a use selects an action button representing the font size, the application will randomly select a number from 6-24 of the font size. Thus, the font size of the text in the subsequent popup will be a randomly selected number 6-24.

The second algorithm includes creating an Attribute Database to store the possible instantiations for each Attribute Category.

In the third algorithm, the prompt displays text ("Prompt Text") called from a Text Database, and the prompt may be closed after (1) a designated period of time to ensure that the user has read the text, and/or (2) the user selects one of two Action Buttons, which appear on the prompt only after the designated period of time.

In the fourth algorithm, each of the Action Buttons identify a change in the instantiation of a different Attribute Category. For example, a first Action Button may result in a change of the prompt shape to an oval while the second Action Button may result in a change of the accompanying sound to "Twinkle, Twinkle, Little Star."

In the fifth algorithm, the language present for each Action Button ("Action Button Language") corresponds to a set of multiple instantiations within a given Attribute Category, one of which will be selected randomly, so that the user will not know exactly what the instantiation will be, although the instantiation is suggested by the language of the Action Button. For example, if an Action Button reads "See Something Funny," an image will be randomly selected from a set that includes, for example, a baby eating a puppy's food while the puppy watches sadly, a man jumping out of a window only to be caught by a bird, and many other options.

FIG. 4 illustrates a flowchart of one or more aspects of an embodiment of the present invention. Provided may be a method for increasing mobile application user engagement in a remote digital therapeutic computing environment, the method comprising, step 402, presenting a first popup window to a user including a plurality of action buttons, step 404, a first of the plurality of action buttons causing a change in a first attribute category to a first instantiation, and, step 406, a second of the plurality of action buttons causing a change in a second attribute category to a second instantiation, the first attribute category and the second attribute category comprising a type of attribute category of a second popup window; and, step 408, subsequent to the presenting the first popup window to the user, presenting the second popup window to the user including a first instantiation if the first of the first plurality of action buttons was selected by the user, and, step 410, a second instantiation if the second of the first plurality of action buttons was selected by the user, wherein the first and second instantiations are presented according to a digital therapeutic program.

While this invention has been described in conjunction with the embodiments outlined above, many alternatives, modifications and variations will be apparent to those skilled in the art upon reading the foregoing disclosure. Accordingly, the embodiments of the invention, as set forth above, are intended to be illustrative, not limiting. Various changes may be made without departing from the spirit and scope of the invention.

What is claimed is:

1. A computer system for increasing mobile application user engagement in a remote digital therapeutic computing environment on an electronic device comprising one or more processors, one or more computer-readable memories, and one or more computer-readable storage devices, and program instructions stored on at least one of the one or more storage devices for execution by at least one of the one or more processors via at least one of the one or more memories, the stored program instructions comprising:

presenting a first popup window to a user including a plurality of action buttons, a first of the plurality of action buttons causing a change in a first attribute category to a first instantiation, and a second of the plurality of action buttons causing a change in a second attribute category to a second instantiation, the first attribute category and the second attribute category comprising a type of attribute category of a second popup window;

subsequent to the presenting the first popup window to the user, presenting the second popup window to the user including a first instantiation if the first of the first plurality of action buttons was selected by the user, and a second instantiation if the second of the first plurality of action buttons was selected by the user, wherein the first and second instantiations are presented according to a digital therapeutic program, and responsive to detecting a deviation, presenting a deviation popup comprising a message to the user, wherein the deviation is determined according to the user's interaction with any of the first and second interfaces.

2. The mobile application user engagement system according to claim 1, wherein at least one of the first instantiation and the second instantiation is determined randomly.

3. The mobile application user engagement system according to claim 1, wherein, in the presenting of the first popup window, the plurality of action buttons are displayed on the first popup window after a predetermined period of time after the first popup window is displayed to the user.

4. The mobile application user engagement system according to claim 1, wherein, in the presenting of the first popup window, the plurality of action buttons are activated on the first popup window after a predetermined period of time after the first popup window is displayed to the user.

5. The mobile application user engagement system according to claim 1, wherein the type of attribute category comprises font color.

6. The mobile application user engagement system according to claim 1, wherein the type of attribute category comprises prompt shapes.

7. The mobile application user engagement system according to claim 1, wherein the type of attribute category comprises prompt movements.

8. The mobile application user engagement system according to claim 1, wherein the type of attribute category comprises prompt opacity.

9. The mobile application user engagement system according to claim 1, wherein the type of attribute category comprises background color.

10. The mobile application user engagement system according to claim 1, wherein the message is selected from a library containing alerts that warn the user of their behavior, information on the importance of adhering to their treatment, and humorous messages.

11. A computer implemented method for increasing mobile application user engagement in a remote digital therapeutic computing environment, the method comprising:

presenting a first popup window to a user including a plurality of action buttons, a first of the plurality of action buttons causing a change in a first attribute category to a first instantiation, and a second of the plurality of action buttons causing a change in a second attribute category to a second instantiation, the first attribute category and the second attribute category comprising a type of attribute category of a second popup window;

subsequent to the presenting the first popup window to the user, presenting the second popup window to the user including a first instantiation if the first of the first plurality of action buttons was selected by the user, and a second instantiation if the second of the first plurality of action buttons was selected by the user, wherein the first and second instantiations are presented according to a digital therapeutic program; and responsive to the user selecting any of the first or second plurality of action buttons, determining a feedback method for promoting engagement of the user wherein the feedback method comprises displaying a message to the user, wherein the message displayed is a type of message determined to engage with the user.

12. The mobile application user engagement method according to claim 11, wherein the first instantiation is determined randomly.

13. The mobile application user engagement method according to claim 11, wherein, in the presenting of the first popup window, the plurality of action buttons are displayed on the first popup window after a predetermined period of time after the first popup window is displayed to the user.

14. The mobile application user engagement method according to claim 11, wherein, in the presenting of the first popup window, the plurality of action buttons are activated on the first popup window after a predetermined period of time after the first popup window is displayed to the user.

15. The mobile application user engagement method according to claim 11, wherein the type of attribute category comprises font color.

16. The mobile application user engagement method according to claim 11, wherein the type of attribute category comprises prompt shapes.

17. The mobile application user engagement method according to claim 11, wherein the type of attribute category comprises prompt movements.

18. The mobile application user engagement method according to claim 11, wherein the type of attribute category comprises prompt opacity.

19. The mobile application user engagement method according to claim 11, wherein the type of attribute category comprises background color.

20. The mobile application user engagement method according to claim 11, wherein the message is selected from a group consisting of alert messages, information messages, and humor messages that would promote user engagement with the system.

* * * * *

UNITED STATES PATENT AND TRADEMARK OFFICE
CERTIFICATE OF CORRECTION

| | | |
|---|---|---|
| PATENT NO. | : 12,142,374 B2 | Page 1 of 1 |
| APPLICATION NO. | : 17/286031 | |
| DATED | : November 12, 2024 | |
| INVENTOR(S) | : Katie Nicole Rodammer | |

It is certified that error appears in the above-identified patent and that said Letters Patent is hereby corrected as shown below:

In the Claims

Column 38, Line 55:
In Claim 10, delete "a library containing alerts that warm the user of their" and insert --a library containing alerts that warn the user of their--

Signed and Sealed this
Eleventh Day of March, 2025

Coke Morgan Stewart
*Acting Director of the United States Patent and Trademark Office*